United States Patent
Chou et al.

(10) Patent No.: US 10,955,334 B2
(45) Date of Patent: Mar. 23, 2021

(54) OPTICAL TRANSMISSION SAMPLE HOLDER AND ANALYSIS, PARTICULARLY FOR HEMOGLOBIN

(71) Applicant: Essenlix Corporation, Monmouth Junction, NJ (US)

(72) Inventors: Stephen Chou, Princeton, NJ (US); Wei Ding, East Windsor, NJ (US); Ji Qi, Skillman, NJ (US); Jun Tian, Belle Mead, NJ (US); Wu Chou, Basking Ridge, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 16/771,502

(22) PCT Filed: Dec. 14, 2018

(86) PCT No.: PCT/US2018/065874
§ 371 (c)(1),
(2) Date: Jun. 10, 2020

(87) PCT Pub. No.: WO2019/118941
PCT Pub. Date: Jun. 20, 2019

(65) Prior Publication Data
US 2020/0378886 A1    Dec. 3, 2020

Related U.S. Application Data
(60) Provisional application No. 62/598,899, filed on Dec. 14, 2017.

(51) Int. Cl.
*G01N 21/03* (2006.01)
*G01N 1/28* (2006.01)
(Continued)

(52) U.S. Cl.
CPC ....... *G01N 21/0303* (2013.01); *G01N 1/2813* (2013.01); *G01N 21/25* (2013.01);
(Continued)

(58) Field of Classification Search
CPC .. G01N 21/0303; G01N 1/2813; G01N 21/25; G01N 21/6458; G01N 33/49;
(Continued)

(56) References Cited

U.S. PATENT DOCUMENTS 4,022,521 A    5/1977  Hall et al.
5,309,213 A *  5/1994  Desjardins ........... G01N 21/534
                                              356/246

(Continued)

FOREIGN PATENT DOCUMENTS

WO    2016090407 A1    6/2016
WO    2017048871 A1    3/2017

OTHER PUBLICATIONS

Written Opinion for PCT/US18/65874 established by ISA/US dated Dec. 30, 2019.

*Primary Examiner* — Roy M Punnoose

(57) ABSTRACT

Among other things, the present invention is related to devices and methods for improving optical analysis of a thin layer of a sample sandwiched between containing between two plates.

84 Claims, 12 Drawing Sheets

(51) Int. Cl.
  *G01N 21/25*   (2006.01)
  *G01N 21/64*   (2006.01)
  *G01N 33/49*   (2006.01)
(52) U.S. Cl.
  CPC ......... *G01N 21/6458* (2013.01); *G01N 33/49*
       (2013.01); *G01N 2021/035* (2013.01); *G01N*
            *2021/6439* (2013.01); *G01N 2201/0221*
                                                (2013.01)
(58) Field of Classification Search
  CPC ..... G01N 2021/035; G01N 2021/6439; G01N
                                            2201/0221
  USPC ....................................................... 356/246
  See application file for complete search history.

(56) References Cited

U.S. PATENT DOCUMENTS

| | | | |
|---|---|---|---|
| 6,180,314 B1 | 1/2001 | Berndt | |
| 8,004,670 B2 * | 8/2011 | Juhl | ................... G01N 21/0303 |
| | | | 356/246 |
| 2007/0087442 A1 | 4/2007 | Wardlaw | |
| 2013/0323858 A1 * | 12/2013 | Abdulhalim | ......... G01N 21/554 |
| | | | 436/501 |
| 2018/0202928 A1 * | 7/2018 | Abdulhalim | ....... G01N 21/4788 |
| 2020/0158626 A1 * | 5/2020 | Watanabe | .............. G01N 30/74 |

* cited by examiner

OPTICAL TRANSMISSION SAMPLE HOLDER AND ANALYSIS, PARTICULARLY FOR HEMOGLOBIN

CROSS REFERENCE

This application is a National Stage entry (§ 371) application of International Application No. PCT/US18/65874, filed on Dec. 14, 2018, which claims the benefit of U.S. Provisional Patent Application No. 62/598,899, filed on Dec. 14, 2017, the contents of which are relied upon and incorporated herein by reference in their entirety.

The entire disclosure of any publication or patent document mentioned herein is entirely incorporated by reference.

FIELD

The present disclosure is related to devices and methods for improving optical transmission analysis of a thin layer of a sample sandwiched between containing between two plates.

BACKGROUND

An optical absorption by a thin layer of a sample is one of the methods to assay a biological and chemical sample. One way to measure an optical absorption is to measure the intensity of the incident light and the transmitted light that directly goes in and out of a sample, respectively.

However, in many practical situations, it can be difficult to directly measure these light intensities, because of various reasons. One reason is that a thin layer sample often needs a sample holder for a measurement and the transmitted light being measured is the light that goes through both the sample and the sample holder. Hence, there is a need for a method that can separate the light absorption by the sample holder from that by the sample.

Another reason is that the incident light and transmitted light are on the opposite side of a sample, it is difficult to use a single detector to both light. Hence, there is a need for using a single photodetector for an absorption measurement.

In prior approaches of optical transmission measurement of a thin sample, a sample holder that comprises two plates has been used to sandwich a sample into a thin layer between the two plates, and the light transmission through an air bubble inside the sample thin layer (which can occur under certain conditions) was used as a reference signal to separate the light absorption by the sample holder from that by the sample. This approach also allow an optical absorption measurement with a single photodetector. In the method, it assumes that (i) light transmission through the air bubble area is the same as that through a zero thickness sample, and (ii) light absorption by the sample holder is the same in the air bubble area (where the reference signal is measured) and in the sample area (where the sample single is measured). However, in reality, both assumptions can be wrong. An air bubble can be generated significantly away from the location of the sample signal, so that there is a significant difference in sample holder absorptions between two locations. The air bobble can be too small, so that light will be significantly scattered and the reference signal is significantly different from a sample having zero thickness. Furthermore, the air bubble generation is random in both occurrences (can or cannot occur) and the location (e.g., random locations).

Accordingly, an object of the present invention to provide the devices and methods to generate the reference light, simplify the optical transmission measurement, and simplify a sample handling. The present invention can overcome or reduce the disadvantages of the prior devices or systems.

BRIEF SUMMARY

Among other things, the present invention is related to devices and methods for improving optical analysis of a thin layer of a sample sandwiched between containing between two plates, particularly, for generating a reference signal that can improve the optical analysis, and for an application of assaying hemoglobin.

A property (e.g. a biological or chemical property) of a sample can be determined by the optical density (i.e. OD) of the sample by the ratio of the intensity of the transmitted light through a thin sample layer to the incident light (i.e. the Beer-Lambert's Law). However, a thin layer sample often needs a sample holder for a measurement, and the light being measured also goes through the sample holder. There is a need to separate the optical transmission signal and optical absorption (e.g. optical density) of a sample from the total transmitted light, which include the light transmission through the sample and through the sample holder.

One objective of the present invention provides the devices and methods of certain embodiments of a sample holder and the use of that improves the optical transmission measurements.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A skilled artisan will understand that the drawings, described below, are for illustration purposes only. In some Figures, the drawings are in scale. In the figures that present experimental data points, the lines that connect the data points are for guiding a view of the data only and have no other means. For clarity purposes, some elements are enlarged when illustrated in the Figures. It should be noted that the Figures do not intend to show the elements in strict proportion. The dimensions of the elements should be delineated from the descriptions herein provided and incorporated by reference. The drawings are not intended to limit the scope of the present invention in any way.

DETAILED DESCRIPTION

Figure 1A:
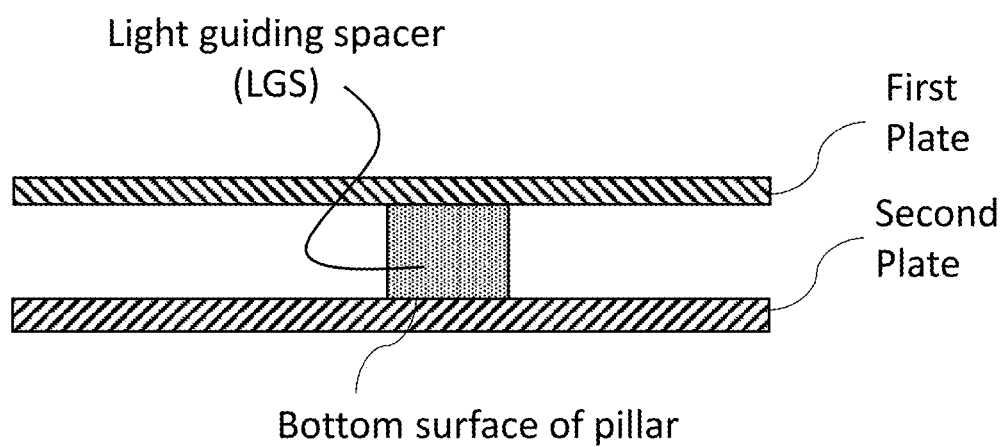
FIG. 1A illustrates a cross-section view of one embodiment of a sample holder, termed OAC (e.g. optical analysis card), for analyzing an analyte in a sample (e.g. hemoglobin in a blood sample) by optical transmission using light, comprising: a first plate, a second plate, and a light guiding spacer (LGS); wherein the LGS has a pillar shape, is sandwiched between the two plates with each end of the pillar in direct contact to one of the plates forming a LGS-plate contact area, and is configured to allow the light transmits from the first plate, through the LGS, to the second plate without going through a sample.

The following detailed description illustrates certain embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "light guiding spacer" or "LGS' can refer to a pillar that, during an optical transmission measurement of a sample, has one end of the pillar in direct contact to a first plate and the other end of the pillar in direct contact of a second plate, In certain embodiments, the first plate and the second plate sandwich the sample between the two plates. In certain embodiments, the optical index and the size of the pillar are predetermined and known. In certain embodiments, the LGS is made of the same material as one or both of the plate. In certain embodiments, the LGS is bond, mold, imprinted, or other ways to connected to one or both plate.

The term "no significant amount of sample" can refer to an amount of sample that is insignificant to an optical transmission measurement of the sample when the measurement is performed in an area that has the two plates and the sample.

The term "LGS-Plate contact areas" can refer to the area in each end of the LGS (which has a pillar shape) that is in direct contact to one of the plates. In certain embodiments, the LGS and one plate is made in one piece of a material, then the LGS-Plate contact area for the end of the LGS connected to the plate is the cross-section of the LGS. In certain embodiments, the LDG and both plates are made of a single piece of material, then the LGS-Plate contact area for both end of the LGS is the cross-section of the LGS.

The terms "lateral cross-section of the LGS" can refer to that a cross-section of a LGS that is parallel with the plates when the LGS is sandwiched between the two plates.

The terms of "the LGS-contact area or a lateral cross-section of the LGS are larger than the wavelength of the light" can refer to that the LGS-contact area or a lateral cross-section of the LGS are larger than the wavelength of the light is larger than the area of disk that has a diameter equal to the wavelength of the light.

The terms "OTSA" means optical transmission sample analysis, that measures the optical density of a thin sample layer by optical transmission.

The term "a SR region" or "a pair of SR region", which are interchangeable, can refer to one sampling region and one corresponding reference region, where an OD of a thin sample layer is determined by taking a ratio of the intensities of the light transmitted through the sample region and through the reference region.

The term "reference region" of an OAC device can refer to the region of the device where light of a wavelength and a polarization goes through the first plate, the light-guiding spacer, and the second plate, wherein the light guiding spacer is a direct contact of the first and second plates. The term "reference region" of an OAC device can refer to the region of the device where a light guiding spacer is sandwich between the two plates and has a direct contact respectively to each plate, wherein, in the reference region, a probing light transmits through, in sequence, the first plate, the light-guiding spacer, and the second plate, without going through the sample.

The term "sampling region" of an OAC device can refer to the region of the device where the light of the sample wavelength and the polarization, that goes through the reference region, goes through the first plate, a sample between the two plates, and the second plate without going through the light guiding spacer.

The term "sampling region" of an OAC device can refer to the region of the device where the sample is between the two plates without a LGS in that region; namely, in the sampling region, a probing light transmits through, in sequence, the first plate, a sample between the two plates, and the second plate without encountering LGS.

The term "distance between the sampling region and the reference region" of an OAC device can refer to the shortest separation between the boundary of reference region and the boundary of the sampling region.

The terms "imager" and "camera" are interchangeable.

The terms a pillar, a LSG or an object "inside a sample" means that the sidewall of the pillar, the LSG, or the object is surrounded by the sample.unifor The term "imprinted" means that a spacer and a plate are fixed monolithically by imprinting (e.g. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together. The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" can refer to one of the two plates in a CROF card, wherein the spacers are fixed to this plate. More descriptions of the COF Card, CROF Card, and X-plate are given in the provisional application serial nos. 62/456,065, filed on Feb. 7, 2017, which is incorporated herein in its entirety for all purposes.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card can refer to the surface of the plate that touches the sample, while the other surface (that does not touch the sample) of the plate is termed "outer surface".

The term "height" or "thickness" of an object in a QMAX process can refer to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process can refer to, unless specifically stated, the area of the object that is parallel to a surface of the plate. For example, spacer area is the area of the spacer that is parallel to a surface of the plate.

The term of QMAX card can refer the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" can refer to the property of the hinge, which substantially maintains an angle between the two plates, after an external force that moves the plates from an initial angle into the angle is removed from the plates.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible. One skilled artisan will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

PRINCIPLES AND CERTAIN EXAMPLES

One objective of the present invention is related to devices and methods for improving optical transmission analysis of a thin layer of a sample sandwiched between containing between two plates, particularly, for generating a reference signal that can improve the optical analysis, and for an application of assaying an analyte in a sample, e.g. hemoglobin in a blood sample.

Certain biological or chemical properties of a sample can be determined by measuring the absorption coefficient of a thin sample layer, $\alpha_s$, in a light transmission experiment through the sample layer. Using Beer-Lambert's Law, the light absorption coefficient of a thin sample layer, $\alpha_s$, is related to the incident light intensity (i.e. the light incident to the sample), $I_i$, and the transmitted light intensity (i.e. the light goes through the sample), $I_t$:

$$OD = \ln\left(\frac{I_i}{I_t}\right) = \alpha_s L_s,$$

where $L_s$ is the length (i.e. thickness) of the sample layer, and OD is the optical density through the sample layer. The light absorption coefficient of a thin sample layer, $a_s$, can be related a property of the sample. Therefore, using the Beer-Lambert's Law, one can determine a property of a sample by measuring the OD of a sample layer.

However, in practice, it is hard to directly measure the intensity of both incident light (i.e. the light directly incident to a sample layer) and transmitted light (i.e. the light directly transmitted through the sample). Typically, what is measured in experiments are the total light transmission through both the sample and the sample holder (This is because a thin layer sample often needs a sample holder for a measurement, and the light being measured also goes through the sample holder). Therefore, there is a need to separate/determine the OD of a sample from the total light transmission.

According to the present invention, a particular sample holder, termed OAC (i.e. optical analysis card), is provided, and an optical density of a material is determined by taking a ratio of the intensities of two transmitted lights: one is the light that transmits through the sampling region of the sample holder, and the other is the light that transmits through the reference region of the sample holder, wherein the OD of the sample is determined without directly measuring the incident light.

Sample Holders

Figure 1B:
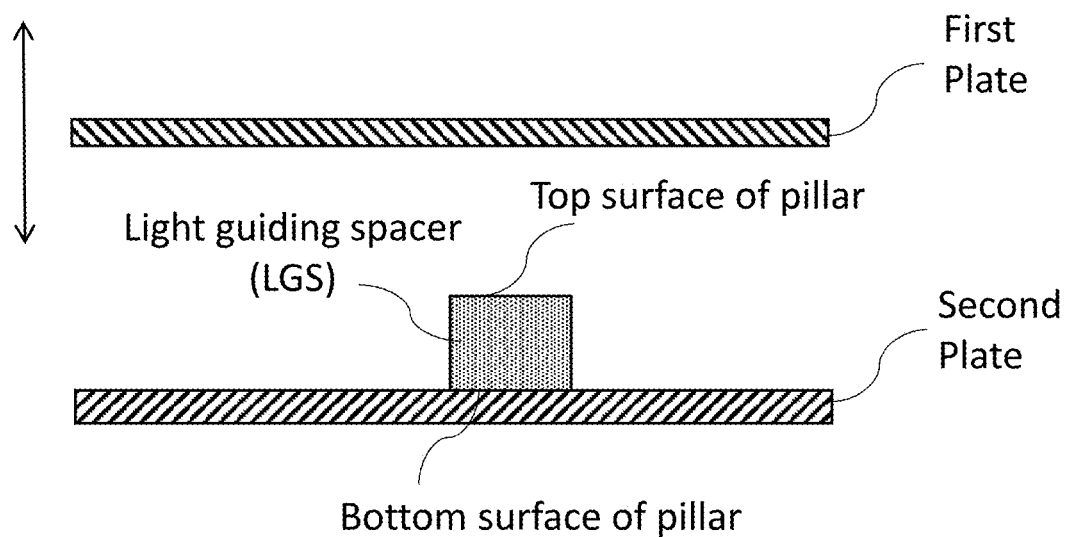
FIG. 1B illustrates a cross-section view of one embodiment of a sample holder, termed OAC (e.g. optical analysis card), for analyzing an analyte in a sample (e.g. hemoglobin in a blood sample) by optical transmission using light, comprising: a first plate, a second plate, and a light guiding spacer (LGS), wherein the two plates are movable relative to each other and the pillar has flat top.
Figure 1C:
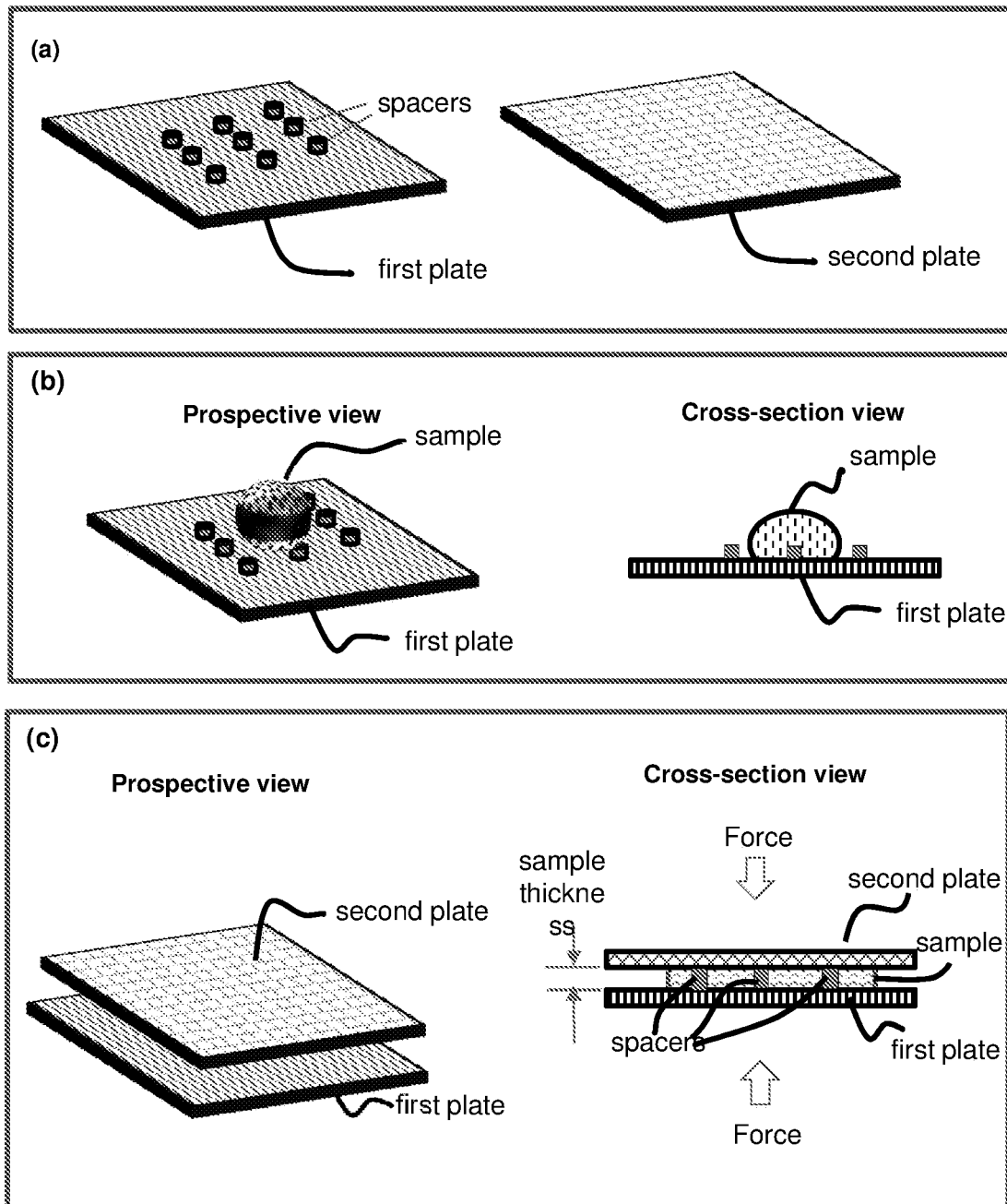
FIG. 1C is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).
Figure 2A:
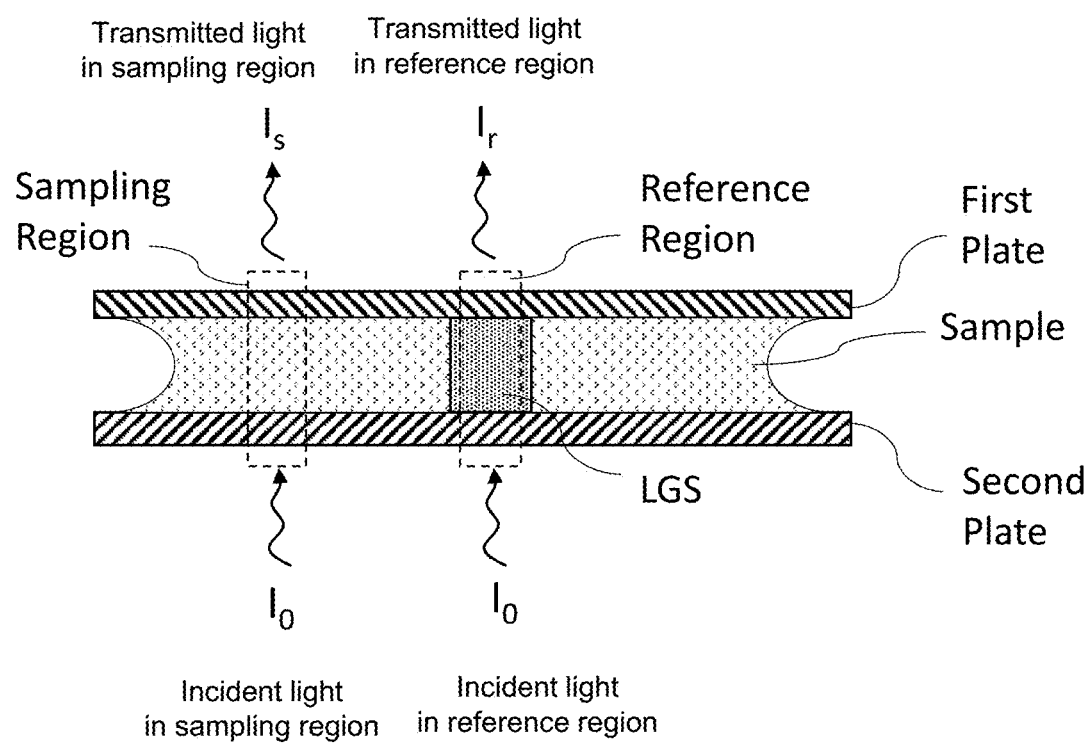
FIG. 2A illustrates a cross-section view of one embodiment of a sample holder with a first plate, second plate and a LGS, a sample in the holder, locations of a sampling region and a reference region, and incident light and transmitted light in the sample region and the reference region respectively
Figure 2B:
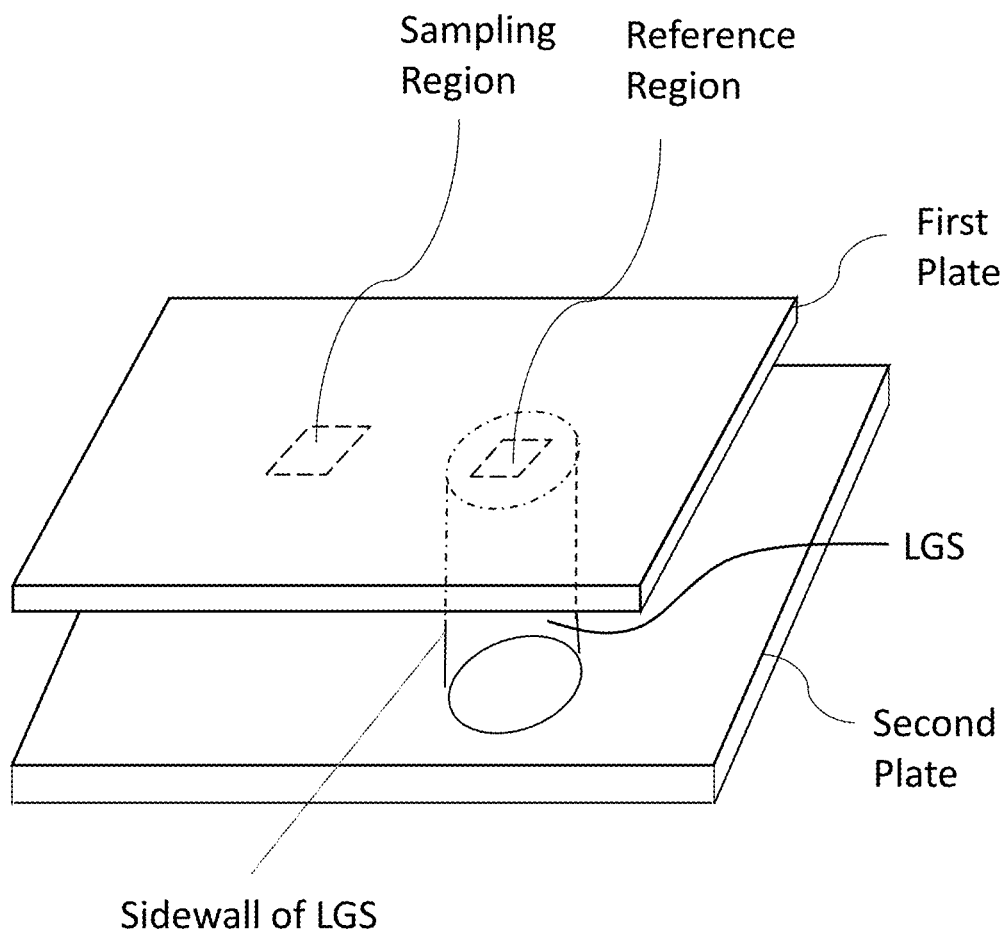
FIG. 2B illustrates a perspective view of one embodiment of a sample holder with a first plate, second plate and a LGS, a sample in the holder, and locations of a sampling region and a reference regions.
Figure 3:
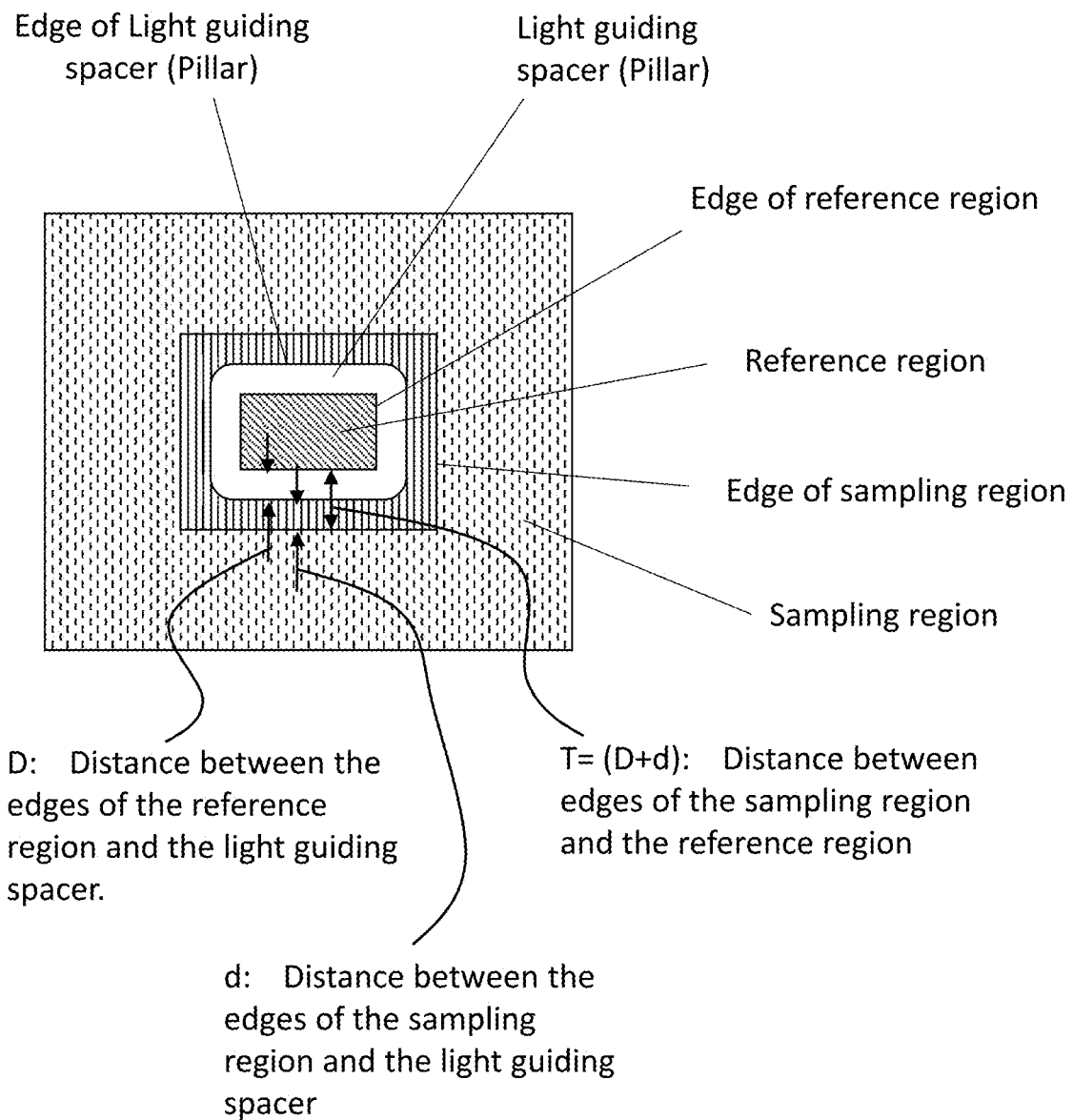
FIG. 3 illustrates a top view of one embodiment of a sample holder with a first plate, second plate and a LGS, location of a LGS, a sampling region, a reference region, and an exemplary location of the edge of the reference region and the sample region. Note that the edges are selected during an imaging processing.

According to the present invention, as shown in FIGS. 1 and 2, one embodiment of a sample holder, termed OAC (i.e. optical analysis card), for analyzing an analyte in a sample (e.g. hemoglobin in a blood sample) by optical transmission using light, comprising:

a first plate, a second plate, a light guiding spacer (LGS), a sampling region, and a reference region, wherein:
  (i) the first plate and second plate are configured to sandwich a sample, this is for an optical transmission analysis by light, into a thin layer between the plates, and each plate has a sample contact area on its inner surface that contacts the sample;
  (ii) the light-guiding spacer (LGS) has a pillar shape, is sandwiched between the two plates with each end of the pillar in direct contact to one of the plates forming a LGS-plate contact area, and is configured to allow the light transmits from the first plate, through the LGS, to the second plate without going through a sample,
  (iii) the sampling region is the region that the light can go through, in sequence, the first plate, the sample, and the second plate, wherein the sampling region does not have the LGS; and
  (iv) the reference region is the region that the light transmits through, in sequence, the first plate, the light-guiding spacer, and the second plate, without going through the sample;

wherein the LGS-contact areas and a lateral cross-section of the LGS are larger than the wavelength of the light, wherein the light-guiding spacer is surrounded by or near the sample; and wherein the sample in the sampling region has a thickness of 500 um or less.

At least a portion of the plates in the reference region and the sampling region are light transmissive.

According to the present invention, as shown in FIGS. 1 and 2, a sample holder, termed OAC (i.e. optical analysis card), has at least a "sampling region" and a "reference region", and the sample layer light absorption coefficient is determined by taking a ratio of the light transmitted through the sampling region to that transmitted through the reference region.

In some embodiments, the sample holder (also termed device) further comprises a plurality of light guiding spacers, that have substantially uniform height, and wherein at least one of the light-guiding spacers is inside the sample contact area.

In some embodiments, the first plate and the second plate are fixed with the LGS (FIG. 1A). In some embodiments, as shown in FIG. 1B, the first plate and the second plate are movable relative to each other into different configurations including an open configuration and a closed configuration. In an open configuration, the plates are separated a part and a sample is deposited. In a closed configuration, the first and second plate is respectively in touch with a flat end of the LGS.

In some embodiments, the first plate and the second plate in the sample regions and the references have uniform thickness, and are light transmissive.

The materials of the plates are plastics, glass, or other materials described by the disclosure.

In some embodiments, other spacers are used to regulate the spacing between the first plate and the second plate, and hence the sample thickness.

Sample OD Measurement Methods.

According to the present invention, a properties of the sample is determined by measuring the OD of a thin layer of the sample, where the OD is determined from the ratio of the light transmitted through the sampling region of OAC to that transmitted through the reference region of OAC.

In some embodiments, the image of a sample in a sample holder is take by a camera and analyzed. (e.g. FIG. 5)

In some embodiments, the wavelength of the light is in the range of 500 nm to 1200 nm, 200 nm to 3000 nm, 3000 nm to 30,000 nm, or 100 nm to 200 nm.

A) Light absorption through a sample determined by light transmissions in sampling and reference regions For the light with an incident light intensity, $I_0$, the transmitted light intensity through a sample, $I_s$ is, using Beer-Lambert's Law, given by:

$$OD_s = \ln\left(\frac{I_0}{I_s}\right) = \varepsilon_s c L_s,$$

where, $\varepsilon_s$ is the extinction coefficient of the sample (e.g. hemoglobin), c is the average concentration of the sample (e.g. hemoglobin), and L is the length of light path through the sample. (E in cm$^{-1}$/M, c in M, L in cm), and $OD_s$ can refer to the optical density through sample.

For the light with an incident light intensity, $I_0$, the transmitted light intensity through a light-guiding spacer of a length $L_r$, $I_r$, is, using Beer-Lambert's Law, given by:

$$OD_r = \ln\left(\frac{I_0}{I_r}\right) = \alpha_r L_r,$$

where $\alpha_r$ is the absorption coefficient of the light-guiding spacer, and L is the length of light path through the sample, and $OD_S$ can refer to the optical density through the light guiding spacer, which is used as a reference.

Subtracting the first equation by the second equation leads to:

$$OD_s - OD_r = \ln\left(\frac{I_0}{I_s}\right) - \ln\left(\frac{I_0}{I_r}\right) = \ln\left(\frac{I_r}{I_s}\right) = \varepsilon_s c L_s - \alpha_r L_r$$

According to the present invention, the above equation shows that the absorption coefficient of a sample layer can be determined by taking a ratio of the transmitted light through the sampling region to that through the reference region, without measuring the incident light (assuming the incident light in the two regions are significantly the same).

Forming uniform thin sample layer using spacers.

FIG. 1 is an illustration of a CROF (Compressed Regulated Open Flow) embodiment. Panel (a) illustrates a first plate and a second plate wherein the first plate has spacers. Panel (b) illustrates depositing a sample on the first plate (shown), or the second plate (not shown), or both (not shown) at an open configuration. Panel (c) illustrates (i) using the two plates to spread the sample (the sample flow between the plates) and reduce the sample thickness, and (ii) using the spacers and the plate to regulate the sample thickness at the closed configuration. The inner surface of each plate may have one or a plurality of binding sites and or storage sites (not shown).

B) Two Kinds of Hemoglobin

There are two kinds of hemoglobin in blood. Oxygenated hemoglobin [HbO$_2$] is the form of hemoglobin with the bound oxygen while deoxygenated hemoglobin [Hb] is the form of hemoglobin without the bound oxygen. Typically, oxygenated hemoglobin [HbO$_2$] is around 75% in vein and 90% in artery.

Total hemoglobin concentration=[HbO$_2$]+[Hb].

Figure 4:
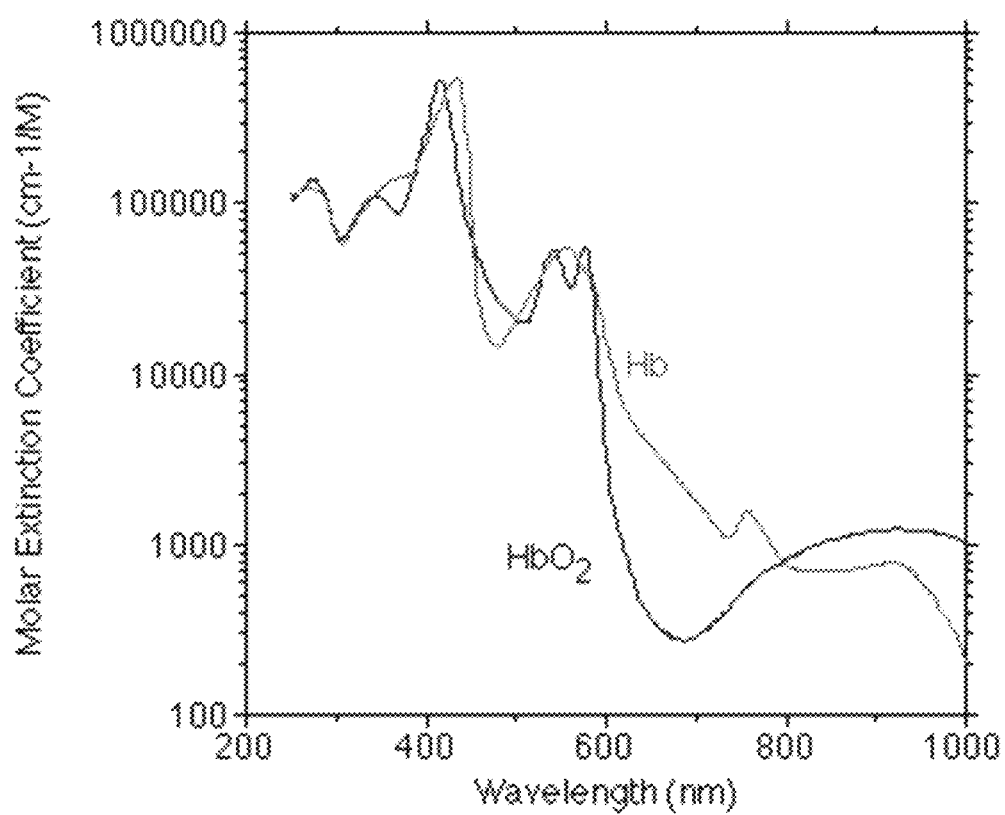
FIG. 4 illustrates the molar extinction coefficient of Oxygenated hemoglobin [$HbO_2$] and deoxygenated hemoglobin [Hb] at wavelength 200 nm to 1000 nm.

Two kinds of hemoglobin can have different extinction coefficient (i.e. light absorption) at different wavelengths as shown in FIG. 4. Therefore, by measuring the light absorption of blood over a different wavelength range, the concentration of the [HbO$_2$] and [Hb] in the blood can be determined, respectively.

C) Optical Transmission Sample Analysis by Comparing the Light Transmission from the Sampling Region and from the Reference Region According to the present invention, the light absorption (and optical density ("OD")) through a thin sample layer is measured by comparing the light transmission from the sample region and from the reference region.

In some cases, the comparison is taking ratio of the light transmission from the sample region to the reference region.

D) Improved Optical Transmission Sample Analysis

In many real measurement situations, there are many imperfections that can significantly reduce the accuracy of OD measurements. For examples, the sample in a sample holder and/or the sample holder itself can have a non-uniform thickness. There are defects in the sample or sample holder, such as air bubbles, dust, or others that can an optical transmission different from that through a perfect (i.e. ideal sample). The light intensity may not be uniform in the entire measurement area.

The present invention has a number of ways to reduce errors in an optical transmission sample analysis (OTSA) caused by the imperfection. According to the present invention, to improve the OD measurement accuracy, the following features, devices and methods below (i.e. in section 1.4 and its subsection) are used individually or a combination of thereof.

I. Reduction of Light Scattering by LGS Sidewall and/or LGS-Plate Interface

According to the present invention, in one of the embodiments of the OD measurement methods that measures the light intensity of the sample region and the reference region, and then takes a ratio of the two intensities, the measurement accuracy can be significantly reduced if the light that goes through the reference region has a strong scattering from (a) the LGS sidewall or (b) the LGS, or the light that goes from the sample region has a significant scattering from a nearby LGS sidewall.

To reduce the effects of the light scatting by the LGS sidewall on the light from the reference region, the edge of the reference region used for OD determination should be certain distance away from the LGS sidewall. Since the reference region cannot smaller than that of the wavelength of the light without suffering significant light diffraction, therefore to reduce the effects of the light scatting by the LGS sidewall on the light from the reference region, at least the cross-section of LGS should be larger than the wavelength of the light.

In some embodiments, the edge of the reference region used for OD determination is certain distance away from the LGS sidewall.

In some embodiments, the cross-section of LGS should be larger than the wavelength of the light, and the edge of the reference region used for OD determination is certain distance away from the LGS sidewall.

Similar to the light from the reference region, to reduce the effects of the light scattering on the light from the sampling region, the edge of the sampling region should be a certain distance away from the LGS sidewall.

In some embodiments, the edge of the sampling region used for OD determination is certain distance away from the LGS sidewall.

In some embodiments, the edge of the reference region used for OD determination is certain distance away from the LGS sidewall, and the edge of the sampling region used for OD determination is certain distance away from the LGS sidewall.

In some embodiments, the cross-section of LGS should be larger than the wavelength of the light, the edge of the reference region used for OD determination is certain distance away from the LGS sidewall, and the edge of the sampling region used for OD determination is certain distance away from the LGS sidewall.

II. Areas of Reference Region and Sampling Region, and Distance Between them

In determining an OD of a sample by taking the ratio of the light intensities through the sample region and through the reference region, it assumes that the incident light in each region has the same intensity, or the thickness of the first plate and the second plate and the sample is respectively the same or known in the sampling region and the reference region. However, in many practical optical systems, neither of the above assumption is true, which causes uncertainties (i.e. errors) in determining the OD. For examples, in practice, the intensity of incident light for a sample optical transmission measurement is not uniform, particularly illumination area is large; and the thickness of the first plate, the second plate, and the sample is respectively not the same or known in the sampling region and the reference region, and each may have a significant variation.

According to the present invention, one way to reduce to errors is to limit the areas of the sampling region and the reference region used to determining an OD of the sample, or make the distance between the sampling region and the reference region small while avoiding the light scattering by the LGS sidewall, or both.

In some embodiments, the area of the sampling region and the distance between the sample region and the reference region are a combination of the above the two paragraphs.

III. Multiple Pairs of Sampling Region and Reference Region

Using one pair of sample region and the reference region can lead to a large error. This is because several reasons: (i) since the spatial variation of the thickness of the first plate, the second plate, and the sample is respectively random, just one pair of sample region and reference region may not represent the majority of the sample; and (ii) since the numbers of optical imperfection and their locations are also random, these optical imperfection can occur at the location of the sampling region and/or the reference region, making the sampling region and the reference region pair unusable in OTSA.

To solve these problems, according to the present invention, multiple pairs of the SR regions are used.

In some embodiments, an OAC comprises a plurality of pairs of SR regions, where the distance between the centers of two neighboring SR regions, and the distance is either substantially periodic or aperiodic.

According to the present invention, reagents for facilitating a test were deposited on the inner surface of the plates of an OAC, the reagents include but not limited to staining reagents, surfactants, antibodies, proteins, and nucleic acids.

Light Guiding Pillar (e.g., Spacer)

In some embodiments, the light guiding spacers are substantially periodic in inter spacer distance and predetermined.

Height of the Light Guiding Pillar

In some embodiments, the height of light-guiding spacer is 1 um, 2 um, 5 um, 10 um, 30 um, 50 um, 100 um, 200 um, 500 um, 1,000 um, 2,000 um, 5,000 um, 10,000 um, or in a range between any of the two values.

Periodicity of the Light Guiding Pillar

In some embodiments, spacer are arranged in periodic array with a period of 1 um, 2 um, 5 um, 10 um, 30 um, 50 um, 100 um, 200 um, 500 um, 1,000 um, 2,000 um, 5,000 um, 10,000 um, or in a range between any of the two values.

Geometry of Light Guiding Spacers (LGS)

In some embodiments, the LGS has a pillar shape with its ends substantially flat. In some embodiments, one or both of the ends of the LGS are fixed with one or both of the plates by bonding, fusing, made from a single piece, or other methods that connect LGS to the plates.

In some embodiments, the shape of the lateral cross-section of LGS includes, not limited to circular, rectangle, square, triangle, polygon, alphabets, numbers, or a combination of thereof.

In some embodiments, the average lateral cross-section of each light-guiding spacer (LGS) is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, 500,000 um^2, 1 mm^2, 2 mm^2, 5 mm^2, 10 mm^2, 50 mm^2, or in a range between any of the two values.

In some preferred embodiments, in the average lateral cross-section of each light-guiding spacer is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, or in a range between any of the two values.

In certain preferred embodiments, the average lateral cross-section of each light-guiding spacer is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, or in a range between any of the two values.

In certain preferred embodiments, the average lateral cross-section of each light-guiding spacer is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, or in a range between any of the two values.

In some embodiments, the average lateral cross-section of each light-guiding spacer is larger than the wavelength of the light that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

In certain preferred embodiments, the average lateral cross-section of each light-guiding spacer is larger than the wavelength of the light that goes through the reference region, by 1 fold, 2 fold, 3 fold, 5 fold, 10 fold, 20 fold, 50 fold, 100 fold, 200 fold, 500 fold, or in a range between any of the two values.

Reference Region Geometry

Shape

In some embodiments, the reference region is less than the size of the minimum lateral cross-section of the light guiding pillar. One advantage is to avoid or reduce light scattering the light guiding sidewall to affect the reference signal.

In some embodiments, the minimum distance between the edge of the light guiding spacer and that of the reference region is 1 um (micron), 2 um, 3 um, 5 um, 10 um, 20 um, 30 um, 50 um, 100 um, 200 um, 500 um, 1000 um, or in a range between any of the two values.

In some preferred embodiments, the minimum distance between the edge of the light guiding spacer and that of the reference region is 1 um (micron), 2 um, 3 um, 5 um, 10 um, 20 um, 30 um, 50 um, 100 um, 200 um, or in a range between any of the two values.

In certain preferred embodiments, the minimum distance between the edge of the light guiding spacer and that of the reference region is 1 um (micron), 2 um, 3 um, 5 um, 10 um, 20 um, 30 um, 50 um, or in a range between any of the two values.

In certain preferred embodiments, the minimum distance between the edge of the light guiding spacer and that of the reference region is larger than the wavelength, that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

In certain preferred embodiments, the minimum distance between the edge of the light guiding spacer and that of the reference region is larger than the wavelength, that goes through the sampling region, by 1 fold, 2 fold, 3 fold, 5 fold, 10 fold, 20 fold, 50 fold, 100 fold, 200 fold, 500 fold, 1000 fold, 5000 fold or in a range between any of the two values.

The ratio of the reference region area and the light guiding spacer area is 3/10, 2/5, 1/2, 3/5, 7/10, 4/5, or in a range between any of the two values.

Sampling Region Geometry

In some embodiments, the edge of the sampling region is a distance away from the edge of the light guiding pillar. One advantage is to avoid or reduce light scattering the light guiding sidewall to affect the reference signal.

In some preferred embodiments, the area of the sampling region is 3/5, 7/10, 4/5, 9/10, 1, 11/10, 6/5, 13/10, 7/5, 3/2, or in the range between any of the two values, of the periodic inter spacer distance.

In some preferred embodiments, the distance between the edge of the sampling region and that of the light guiding spacer is 1/5, 3/10, 2/5, 1/2, 3/5, 7/10, 4/5, 9/10, 1, or in the rage between any of the two values, of the light guiding spacer area.

In some preferred embodiments, the distance between the edge of the sampling region and that of the light guiding spacer is larger than the wavelength, that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

In some preferred embodiments, the distance between the edge of the sampling region and that of the light guiding spacer is larger than the wavelength, that goes through the sampling region, by 1 fold, 2 fold, 3 fold, 5 fold, 10 fold, 20 fold, 50 fold, 100 fold, 200 fold, 500 fold, 1000 fold, 5000 fold or in a range between any of the two values.

Distance Between Sampling Region and Reference Region

In some embodiments, the distance between the edge of sampling area and the reference region is 1 um (micron), 2 um, 3 um, 5 um, 10 um, 20 um, 30 um, 40 um, 50 um, 100 um, 200 um, 500 um, 1000 um or in the range between any of the two values.

In certain preferred embodiments, the distance between the edge of sampling area and the reference region is from 30 um (micron) to 50 um, 20 um to 60 um, 10 um to 70 um, 5 um to 75 um, or in the range between any of the two values.

In certain preferred embodiments, the distance between the edge of sampling area and the reference region is larger than the wavelength, that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

In some embodiments, the distance between the edge of sampling area and the reference region is 2/5, 1/2, 3/5, 7/10, 4/5, 9/10, 1, 11/10, 6/5, 13/10, 7/5, 3/2, 8/5, 17/10, or in the range between any of the two values, of the light guiding spacer area.

In some embodiments, the distance between the edge of sampling area and the reference region is larger than the wavelength of the light that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

In some embodiments, the distance between the edge of sampling area and the reference region is larger than the wavelength, that goes through the sampling region, by 1 fold, 2 fold, 3 fold, 5 fold, 10 fold, 20 fold, 50 fold, 100 fold, 200 fold, 500 fold, 1000 fold, 5000 fold or in a range between any of the two values.

Lysing Reagent Coating for iMOST-HgB Device

In some embodiment, surfactant is coated on the plate and dissolved into the blood to achieve a uniform distribution of red blood cell in device, wherein the coating can be on first plate, or second plate, or both.

In some embodiment, surfactant is coated on the plate and dissolved into the blood to lyse the red blood cell in device, wherein the coating can be on first plate, or second plate, or both.

In some embodiment, the surfactant coated in the device including but not limit to Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, Tween 20, Tween 40, Tween 60, Tween 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, Triton X-100, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiment, the reagent causing red blood cell lysis coated in the device including but not limit to Pluronic F-127, Cremophor EL, Pluronic F-68, Myrj 52, Brij 35, sodium oleate, sodium dodecyl sulfate, Tween 20, Tween 40, Tween 60, Tween 80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

In some embodiment, the anticoagulant coated in the device including but not limit to EDTA such as dipotassium ethylenediaminetetraacetic acid (K2EDTA), tripotassium ethylenediaminetetraacetic (K3EDTA), coumarins (vitamin K antagonists), warfarin (coumadin), acenocoumarol, phenprocoumon, atromentin, phenindione, heparin, fondaparinux and idraparinux, dabigatran, rivaroxaban, apixaban, edoxaban, betrixaban, NOACs, hirudin, lepirudin, bivalirudin, agratroban, dabigatran, batroxobin, hementin, Vitamin E, sodium citrate, acid citrate dextrose, oxalate such as fluoride oxalate, deltaparin, desirudin, enoxaparin.

In some embodiment, to achieve a uniform distribution of red blood cell in device, Zwittergent is coated on the plate with a preferred area concentration of 3 ng/mm$^2$, 5 ng/mm$^2$, 8 ng/mm², 12 ng/mm², 15 ng/mm², 25 ng/mm², 35 ng/mm², 50 ng/mm², 80 ng/mm², 100 ng/mm² or in a range between any of the two values.

In some embodiment, to lyse red blood cell in device, Zwittergent is coated on the plate with a preferred area concentration of 100 ng/mm², 120 ng/mm², 150 ng/mm², 180 ng/mm², 200 ng/mm², 300 ng/mm², 400 ng/mm², 500 ng/mm², 800 ng/mm², 1000 ng/mm² or in a range between any of the two values.

In some embodiment, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiment, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

Measurement Range for iMOST-HgB Device

In some embodiment, the hemoglobin measurement range of the device is between 0 g/dL to 40 g/dL.

In some embodiment, the preferred hemoglobin measurement range of the device is between 0 g/dL to 30 g/dL.

In some embodiment, the preferred hemoglobin measurement range of the device is between 5 g/dL to 26 g/dL.

Scattering Particle Removal and Compensation

In certain situations, there are imperfections that can significantly reduce the accuracy of absorption and/or hemoglobin measurements.

For examples, there are interfering particles in the sample or sample holder, including but not limited to, particles increasing turbidity, light scattering particle, air bubbles, dust, or others that can an optical transmission different from that through a perfect (i.e. ideal sample).

The present invention has a number of ways to reduce errors in an optical transmission sample analysis (OTSA) caused by the imperfection.

In some embodiment, multiple pairs of the SR regions are used. For each pair of the SR region, an OD of a sample is determined by taking the ratio of the light intensities through the sample region and through the reference region. For a given pair of the SR region, a quality measurement of the SR region is calculated; If the quality measurement is low, this pair of the SR region is excluded from the pooling algorithm in the next stage. The pooling algorithm is to pool OD of a sample over all pairs of SR regions. Various pooling algorithm can be utilized, including but not limited to median, mean, max, min, k-means, etc.

In some embodiment, the imperfection areas are removed or excluded from the image before the light intensities analyze.

In some embodiment, the imperfection areas with a boundary are removed or excluded from the image before the light intensities analyze, wherein the boundary size is between 1 um to 50 um; wherein the preferred boundary size is between 5 um to 20 um.

Measurement with/without Scanning

In certain embodiment, one location on device is measured for analysis, particularly for Hemoglobin.

QMAX System

A) QMAX Card

Details of the QMAX card are described in detail in a variety of publications including International Application No. PCT/US2016/046437, which is hereby incorporated by reference herein for all purposes.

I. Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) ae used for the plate to achieve certain objectives.

In certain embodiments, the two plates have the same or different parameters for each of the following parameters: plate material, plate thickness, plate shape, plate area, plate flexibility, plate surface property, and plate optical transparency.

(i) Plate Materials. The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1: The inorganic materials for the plates include, not limited to, glass, quartz, oxides, silicon-dioxide, silicon-nitride, hafnium oxide (HfO), aluminum oxide (AlO), semi-conductors: (silicon, GaAs, GaN, etc.), metals (e.g. gold, silver, coper, aluminum, Ti, Ni, etc.), ceramics, or any combinations of thereof.

Mat-2: The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyimide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain embodiments, the plates are each independently made of at least one of glass, plastic, ceramic, and metal. In certain embodiments, each plate independently includes at least one of glass, plastic, ceramic, and metal.

In certain embodiments, one plate is different from the other plate in lateral area, thickness, shape, materials, or surface treatment. In certain embodiments, one plate is the same as the other plate in lateral area, thickness, shape, materials, or surface treatment.

The materials for the plates are rigid, flexible or any flexibility between the two. The rigid (e.g. stiff) or flexibility is relative to a give pressing forces used in bringing the plates into the closed configuration.

In certain embodiments, a selection of rigid or flexible plate are determined from the requirements of controlling a uniformity of the sample thickness at the closed configuration.

In certain embodiments, at least one of the two plates are transparent (to a light). In certain embodiments at least a part or several parts of one plate or both plates are transparent. In certain embodiments, the plates are non-transparent.

(ii) Plate Thickness. In certain embodiments, the average thicknesses for at least one of the pates are 2 nm or less, 10 nm or less, 100 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, or a range between any two of the values.

In certain embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In certain embodiments, the thickness of a plate is not uniform across the plate. Using a different plate thickness at different location can be used to control the plate bending, folding, sample thickness regulation, and others.

(iii) Plate Shape and Area. Generally, the plates can have any shapes, as long as the shape allows a compress open flow of the sample and the regulation of the sample thickness. However, in certain embodiments, a particular shape can be advantageous. The shape of the plate can be round, elliptical, rectangles, triangles, polygons, ring-shaped, or any superpositions of these shapes.

In certain embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plates is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long it needed. The belt can be rolled into a roll.

(iv) Plate Surface Flatness. In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In certain embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

(v) Plate Surface Parallelness. In certain embodiments, the two surfaces of the plate is significantly parallel with each other. In certain embodiments, the two surfaces of the plate is not parallel with each other.

(vi) Plate Flexibility. In certain embodiments, a plate is flexible under the compressing of a CROF process. In certain embodiments, both plates are flexible under the compressing of a CROF process. In certain embodiments, a plate is rigid and another plate is flexible under the compressing of a CROF process. In certain embodiments, both plates are rigid. In certain embodiments, both plate are flexible but have different flexibility.

(vii) Plate Optical Transparency. In certain embodiments, a plate is optical transparent. In certain embodiments, both plates are optical transparent. In certain embodiments, a plate is optical transparent and another plate is opaque. In certain embodiments, both plates are opaque. In certain embodiments, both plate are optical transparent but have different optical transparency. The optical transparency of a plate can refer to a part or the entire area of the plate.

(viii) Surface Wetting Properties. In certain embodiments, a plate has an inner surface that wets (e.g. contact angle is less 90 degree) the sample, the transfer liquid, or both. In certain embodiments, both plates have an inner surface that wets the sample, the transfer liquid, or both; either with the same or different wettability. In certain embodiments, a plate has an inner surface that wets the sample, the transfer liquid, or both; and another plate has an inner surface that does not wet (e.g. the contact angle equal to or larger than 90 degree). The wetting of a plate inner surface can refer to a part or the entire area of the plate.

In certain embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

II. Spacers (i) Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

(ii) Spacer Architectures and Shapes. To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Certain embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (e.g. the sample flows around and pass the spacer. For example, a post as the spacer.), and the enclosed spacer is the spacer that stop the sample flow (e.g. the sample cannot flow beyond the spacer. For example, a ring shape spacer and the sample is inside the ring.). Both types of spacers use their height to regular the final sample thickness at a closed configuration.

In certain embodiments, the spacers are open-spacers only. In certain embodiments, the spacers are enclosed-spacers only. In certain embodiments, the spacers are a combination of open-spacers and enclosed-spacers.

The term "pillar spacer" means that the spacer has a pillar shape and the pillar shape can refer to an object that has height and a lateral shape that allow a sample to flow around it during a compressed open flow.

In certain embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In certain embodiments, the spacers can be and/or can include posts, columns, beads, spheres, and/or other suitable geometries. The lateral shape and dimension (e.g., transverse to the respective plate surface) of the spacers can be anything, except, in certain embodiments, the following restrictions: (i) the spacer geometry will not cause a significant error in measuring the sample thickness and volume; or (ii) the spacer geometry would not prevent the out-flowing of the sample between the plates (e.g. it is not in enclosed form). But in certain embodiments, they require some spacers to be closed spacers to restrict the sample flow.

In certain embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In certain embodiments, the spacers are pillars of various lateral shapes, sidewalls, and pillar-height to pillar lateral area ratio. In a preferred embodiment, the spacers have shapes of pillars for allowing open flow.

(iii) Spacers' Materials. In the present invention, the spacers are generally made of any material that is capable of being used to regulate, together with the two plates, the thickness of a relevant volume of the sample. In certain embodiments, the materials for the spacers are different from that for the plates. In certain embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

(iv) Spacers' Mechanical Strength and Flexibility. In certain embodiments, the mechanical strength of the spacers are strong enough, so that during the compression and at the closed configuration of the plates, the height of the spacers is the same or significantly same as that when the plates are in an open configuration. In certain embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

(v) Spacers Inside Sample. To achieve desired sample thickness reduction and control, particularly to achieve a good sample thickness uniformity, in certain embodiments, the spacers are placed inside the sample, or the relevant volume of the sample. In certain embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

(vi) Spacer Height. In certain embodiments, all spacers have the same pre-determined height. In certain embodiments, spacers have different pre-determined height. In certain embodiments, spacers can be divided into groups or regions, wherein each group or region has its own spacer height. And in certain embodiments, the predetermined height of the spacers is an average height of the spacers. In certain embodiments, the spacers have approximately the same height. In certain embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 um (e.g. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In certain embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In certain embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in certain embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (e.g. less surface concentration).

(vii) Spacer Lateral Dimension. For an open-spacer, the lateral dimensions can be characterized by its lateral dimension (sometime being called width) in the x and y—two orthogonal directions. The lateral dimension of a spacer in each direction is the same or different. In certain embodiments, the lateral dimension for each direction (x or y) is . . . .

In certain embodiments, the ratio of the lateral dimensions of x to y direction is 1, 1.5, 2, 5, 10, 100, 500, 1000, 10,000, or a range between any two of the value. In certain embodiments, a different ratio is used to regulate the sample flow direction; the larger the ratio, the flow is along one direction (larger size direction).

In certain embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In certain embodiments, all spacers have the same shape and dimensions. In certain embodiments, each of the spacers have different lateral dimensions.

For enclosed-spacers, in certain embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

(viii) Aspect Ratio of Height to the Average Lateral Dimension of Pillar Spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

(ix) Spacer Height Precisions. The spacer height should be controlled precisely. The relative precision of the spacer (e.g. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

(x) Inter-Spacer Distance. The spacers can be a single spacer or a plurality of spacers on the plate or in a relevant area of the sample. In certain embodiments, the spacers on the plates are configured and/or arranged in an array form, and the array is a periodic, non-periodic array or periodic in some locations of the plate while non-periodic in other locations.

In certain embodiments, the periodic array of the spacers has a lattice of square, rectangle, triangle, hexagon, polygon, or any combinations of thereof, where a combination means that different locations of a plate has different spacer lattices.

In certain embodiments, the inter-spacer distance of a spacer array is periodic (e.g. uniform inter-spacer distance) in at least one direction of the array. In certain embodiments, the inter-spacer distance is configured to improve the uniformity between the plate spacing at a closed configuration.

The distance between neighboring spacers (e.g. the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a 10 mm or less, 20 mm or less, 30 mm or less, 50 mm or less, 70 mm or less, 100 mm or less, or any range between the values.

The distance between neighboring spacers (e.g. the inter-spacer distance) is selected so that for a given properties of the plates and a sample, at the closed-configuration of the plates, the sample thickness variation between two neighboring spacers is, in certain embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the accuracy of the inter spacer distance.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (e.g. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

(xi) Spacer Density. The spacers are arranged on the respective plates at a surface density of greater than one per $um^2$, greater than one per 10 $um^2$, greater than one per 100 $um^2$, greater than one per 500 $um^2$, greater than one per 1000 $um^2$, greater than one per 5000 $um^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

(3) the spacers are configured to not take significant surface area (volume) in a given sample area (volume);

(xii) Ratio of Spacer Volume to Sample Volume. In many embodiments, the ratio of the spacer volume (e.g. the volume of the spacer) to sample volume (e.g. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (e.g. flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

(xiii) Spacers Fixed to Plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

In certain embodiments of the present disclosure, spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (e.g. the spacer moves away from its original position on the plate surface).

In certain embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In certain embodiments, a spacer is fixed to a plate monolithically.

In certain embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (e.g. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In certain embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In certain embodiments, at least a distance between two spacers is predetermined ("predetermined inter-spacer distance" means that the distance is known when a user uses the plates.).

In certain embodiments of all methods and devices described herein, there are additional spacers besides to the fixed spacers.

(xiv) Specific Sample Thickness. In present invention, it was observed that a larger plate holding force (e.g. the force that holds the two plates together) can be achieved by using a smaller plate spacing (for a given sample area), or a larger sample area (for a given plate-spacing), or both.

In certain embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

The spacers can be fabricated on a plate in a variety of ways, using lithography, etching, embossing (nanoimprint), depositions, lift-off, fusing, or a combination of thereof. In certain embodiments, the spacers are directly embossed or imprinted on the plates. In certain embodiments, the spacers imprinted into a material (e.g. plastics) that is deposited on the plates. In certain embodiments, the spacers are made by directly embossing a surface of a CROF plate. The nanoimprinting can be done by roll to roll technology using a roller imprinter, or roll to a planar nanoimprint. Such process has a great economic advantage and hence lowering the cost.

In certain embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In certain embodiments, the spacers deposited on the plate are fused with the plate. In certain embodiments, the spacer and the plates are fabricated in a single process. The single process includes imprinting (e.g. embossing, molding) or synthesis.

In certain embodiments, at least two of the spacers are fixed to the respective plate by different fabrication methods, and optionally wherein the different fabrication methods include at least one of being deposition, bonded, fuse, imprinted, and etched.

In certain embodiments, one or more of the spacers are fixed to the respective plate(s) is by a fabrication method of being bonded, being fused, being imprinted, or being etched, or any combination of thereof.

In certain embodiments, the fabrication methods for forming such monolithic spacers on the plate include a method of being bonded, being fused, being imprinted, or being etched, or any combination of thereof.

B) Adaptor

Details of the Adaptor are described in detail in a variety of publications including International Application No. PCT/US2018/017504, which is hereby incorporated by reference herein for all purposes.

The present invention that is described herein address this problem by providing a system comprising an optical adaptor and a smartphone. The optical adaptor device fits over a smartphone converting it into a microscope which can take both fluorescent and bright-field images of a sample. This system can be operated conveniently and reliably by a common person at any location. The optical adaptor takes advantage of the existing resources of the smartphone, including camera, light source, processor and display screen, which provides a low-cost solution let the user to do bright-field and fluorescent microscopy.

In this invention, the optical adaptor device comprises a holder frame fitting over the upper part of the smartphone and an optical box attached to the holder having sample receptacle slot and illumination optics. In some references (U.S. Pat. No. 2016/029091 and U.S. Pat. No. 2011/0292198), their optical adaptor design is a whole piece including both the clip-on mechanics parts to fit over the smartphone and the functional optics elements. This design has the problem that they need to redesign the whole-piece optical adaptor for each specific model of smartphone. But in this present invention, the optical adaptor is separated into a holder frame only for fitting a smartphone and a universal optical box containing all the functional parts. For the smartphones with different dimensions, as long as the relative positions of the camera and the light source are the same, only the holder frame need to be redesigned, which will save a lot of cost of design and manufacture.

The optical box of the optical adaptor comprises: a receptacle slot which receives and position the sample in a sample slide in the field of view and focal range of the smartphone camera; a bright-field illumination optics for capturing bright-field microscopy images of a sample; a fluorescent illumination optics for capturing fluorescent microscopy images of a sample; a lever to switch between bright-field illumination optics and fluorescent illumination optics by sliding inward and outward in the optical box.

The receptacle slot has a rubber door attached to it, which can fully cover the slot to prevent the ambient light getting into the optical box to be collected by the camera. In U.S. Pat. 2016/0290916, the sample slot is always exposed to the ambient light which won't cause too much problem because it only does bright-field microscopy. But the present invention can take the advantage of this rubber door when doing fluorescent microscopy because the ambient light would bring a lot of noise to the image sensor of the camera.

To capture good fluorescent microscopy image, it is desirable that nearly no excitation light goes into the camera and only the fluorescent emitted by the sample is collected by the camera. For all common smartphones, however, the optical filter putting in front of the camera cannot block the undesired wavelength range of the light emitted from the light source of a smartphone very well due to the large divergence angle of the beams emitted by the light source and the optical filter not working well for un-collimated beams. Collimation optics can be designed to collimated the beam emitted by the smartphone light source to address this issue, but this approach increase the size and cost of the adaptor. Instead, in this present invention, fluorescent illumination optics enables the excitation light to illuminate the sample partially from the waveguide inside the sample slide and partially from the backside of the sample side in large oblique incidence angle so that excitation light will nearly not be collected by the camera to reduce the noise signal getting into the camera.

The bright-field illumination optics in the adaptor receive and turn the beam emitted by the light source so as to back-illuminated the sample in normal incidence angle.

Typically, the optical box also comprises a lens mounted in it aligned with the camera of the smartphone, which magnifies the images captured by the camera. The images captured by the camera can be further processed by the processor of smartphone and outputs the analysis result on the screen of smartphone.

To achieve both bright-field illumination and fluorescent illumination optics in a same optical adaptor, in this present invention, a slidable lever is used. The optical elements of the fluorescent illumination optics are mounted on the lever and when the lever fully slides into the optical box, the fluorescent illumination optics elements block the optical path of bright-field illumination optics and switch the illumination optics to fluorescent illumination optics. And when the lever slides out, the fluorescent illumination optics elements mounted on the lever move out of the optical path and switch the illumination optics to bright-field illumination optics. This lever design makes the optical adaptor work in both bright-field and fluorescent illumination modes without the need for designing two different single-mode optical boxes.

The lever comprises two planes at different planes at different heights.

In certain embodiments, two planes can be joined together with a vertical bar and move together in or out of the optical box. In certain embodiments, two planes can be separated and each plane can move individually in or out of the optical box.

The upper lever plane comprises at least one optical element which can be, but not limited to be an optical filter. The upper lever plane moves under the light source and the preferred distance between the upper lever plane and the light source is in the range of 0 to 5 mm.

Part of the bottom lever plane is not parallel to the image plane. And the surface of the non-parallel part of the bottom lever plane has mirror finish with high reflectivity larger than 95%. The non-parallel part of the bottom lever plane moves under the light source and deflects the light emitted from the light source to back-illuminate the sample area right under the camera. The preferred tilt angle of the non-parallel part of the bottom lever plane is in the range of 45 degree to 65 degree and the tilt angle is defined as the angle between the non-parallel bottom plane and the vertical plane.

Part of the bottom lever plane is parallel to the image plane and is located under and 1 mm to 10 mm away from the sample. The surface of the parallel part of the bottom lever plane is highly light absorptive with light absorption larger than 95%. This absorptive surface is to eliminate the reflective light back-illuminating on the sample in small incidence angle.

To slide in and out to switch the illumination optics using the lever, a stopper design comprising a ball plunger and a groove on the lever is used in order to stop the lever at a pre-defined position when being pulled outward from the adaptor. This allow the user to use arbitrary force the pull the lever but make the lever to stop at a fixed position where the optical adaptor's working mode is switched to bright-filed illumination.

A sample slider is mounted inside the receptacle slot to receive the QMAX device and position the sample in the QMAX device in the field of view and focal range of the smartphone camera.

The sample slider comprises a fixed track frame and a moveable arm:

The frame track is fixedly mounted in the receptacle slot of the optical box. And the track frame has a sliding track slot that fits the width and thickness of the QMAX device so that the QMAX device can slide along the track. The width and height of the track slot is carefully configured to make the QMAX device shift less than 0.5 mm in the direction perpendicular to the sliding direction in the sliding plane and shift less than less than 0.2 mm along the thickness direction of the QMAX device.

The frame track has an opened window under the field of view of the camera of smartphone to allow the light back-illuminate the sample.

A moveable arm is pre-built in the sliding track slot of the track frame and moves together with the QMAX device to guide the movement of QMAX device in the track frame.

The moveable arm equipped with a stopping mechanism with two pre-defined stop positions. For one position, the arm will make the QMAX device stop at the position where a fixed sample area on the QMAX device is right under the camera of smartphone. For the other position, the arm will make the QMAX device stop at the position where the sample area on QMAX device is out of the field of view of the smartphone and the QMAX device can be easily taken out of the track slot.

The moveable arm switches between the two stop positions by a pressing the QMAX device and the moveable arm together to the end of the track slot and then releasing.

The moveable arm can indicate if the QMAX device is inserted in correct direction. The shape of one corner of the QMAX device is configured to be different from the other three right angle corners. And the shape of the moveable arm matches the shape of the corner with the special shape so that only in correct direction can QMAX device slide to correct position in the track slot.

C) Smartphone/Detection System

Details of the Smartphone/Detection System are described in detail in a variety of publications including International Application (IA) No. PCT/US2016/046437 filed on Aug. 10, 2016, IA No. PCT/US2016/051775 filed Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, each of which are hereby incorporated herein by reference in their entirety for all purposes.

The devices/apparatus, systems, and methods herein disclosed can include or use Q-cards for sample detection, analysis, and quantification. In certain embodiments, the Q-card is used together with an adaptor that can connect the Q-card with a smartphone detection system. In certain embodiments, the smartphone comprises a camera and/or an illumination source. In certain embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In certain embodiments, the smartphone comprises a camera, but the camera is not used for image capturing.

In certain embodiments, the smartphone comprises a light source such as but not limited to LED (light emitting diode). In certain embodiments, the light source is used to provide illumination to the sample when the sample is positioned in the field of view of the camera (e.g. by an adaptor). In certain embodiments, the light from the light source is enhanced, magnified, altered, and/or optimized by optical components of the adaptor.

In certain embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In certain embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In certain embodiments, the smartphone is an iPhone™, an Android™ phone, or a Windows™ phone.

D) Method of Manufacture

Details of the Method of Manufacture are described in detail in a variety of publications including International Application No. PCT/US2018/057873 filed Oct. 26, 2018, which is hereby incorporated by reference herein for all purposes.

Devices of the disclosure can be fabricated using techniques well known in the art. The choice of fabrication technique will depend on the material used for the device and the size of the spacer array and/or the size of the spacers. Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small spacers and large aspect ratios (ratio of spacer height to lateral dimension). Thermoforming (embossing, injection molding) of plastic devices can also be used, e.g., when the smallest lateral feature is >20 microns and the aspect ratio of these features is 10.

Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) can also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding can be chosen as the method of manufacture. Compression molding (also called hot embossing or relief imprinting) has the advantages of being compatible with high molecular weight polymers, which are excellent for small structures and can replicate high aspect ratio structures but has longer cycle times. Injection molding works well for low aspect ratio structures and is most suitable for low molecular weight polymers.

A device can be fabricated in one or more pieces that are then assembled. Layers of a device can be bonded together by clamps, adhesives, heat, anodic bonding, or reactions between surface groups (e.g., wafer bonding). Alternatively, a device with channels or gaps in more than one plane can be fabricated as a single piece, e.g., using stereolithography or other three-dimensional fabrication techniques.

To reduce non-specific adsorption of cells or compounds released by lysed cells onto the surfaces of the device, one or more surfaces of the device can be chemically modified to be non-adherent or repulsive. The surfaces can be coated with a thin film coating (e.g., a monolayer) of commercial non-stick reagents, such as those used to form hydrogels. Additional examples chemical species that can be used to modify the surfaces of the device include oligoethylene glycols, fluorinated polymers, organosilanes, thiols, polyethylene glycol, hyaluronic acid, bovine serum albumin, poly-vinyl alcohol, mucin, poly-HEMA, methacrylated PEG, and agarose. Charged polymers can also be employed to repel oppositely charged species. The type of chemical species used for repulsion and the method of attachment to the surfaces of the device will depend on the nature of the species being repelled and the nature of the surfaces and the species being attached. Such surface modification techniques are well known in the art. The surfaces can be functionalized before or after the device is assembled. The surfaces of the device can also be coated in order to capture materials in the sample, e.g., membrane fragments or proteins.

In certain embodiments of the present disclosure, a method for fabricating any Q-Card of the present disclosure can comprise injection molding of the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise Laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise injection molding and laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise nanoimprinting or extrusion printing to fabricated both the first and the second plate. In certain embodiments of the present disclosure, a method for fabricating any Q-Card of the present disclosure can comprise fabricating the first plate or the second plate, using injection molding, laser cutting the first plate, nanoimprinting, extrusion printing, or a combination of thereof. In certain embodiments of the present disclosure, a method for fabricating any Q-Card of the present disclosure can comprise a step of attaching the hinge on the first and the second plates after the fabrication of the first and second plates.

E) Sample Types & Subjects

Details of the Samples & Subjects are described in detail in a variety of publications including International Application (IA) No. PCT/US2016/046437 filed on Aug. 10, 2016, IA No. PCT/US2016/051775 filed on Sep. 14, 2016, IA No. PCT/US201/017307 filed on Feb. 7, 2018, IA No. and PCT/US2017/065440 filed on Dec. 8, 2017, each of which is hereby incorporated by reference herein for all purposes.

A sample can be obtained from a subject. A subject as described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of subjects that can benefit is subjects who have or are suspected of having an infection (e.g., a bacterial and/or a viral infection). Another particular class of subjects that can benefit is subjects who can be at higher risk of getting an infection. Furthermore, a subject treated by any of the methods or compositions described herein can be male or female. Any of the methods, devices, or kits disclosed herein can also be performed on a non-human subject, such as a laboratory or farm animal. Non-limiting examples of a non-human subjects include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

The devices, apparatus, systems, and methods herein disclosed can be used for samples such as but not limited to diagnostic samples, clinical samples, environmental samples and foodstuff samples.

For example, in certain embodiments, the devices, apparatus, systems, and methods herein disclosed are used for a sample that includes cells, tissues, bodily fluids and/or a mixture thereof. In certain embodiments, the sample comprises a human body fluid. In certain embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In certain embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In certain embodiments, the devices, apparatus, systems, and methods herein disclosed are used for a foodstuff sample, which is suitable or has the potential to become suitable for animal consumption, e.g., human consumption. In certain embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (uL, also "uL" herein) or less, 500 uL or less, 300 uL or less, 250 uL or less, 200 uL or less, 170 uL or less, 150 uL or less, 125 uL or less, 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the volume of the sample includes, but is not limited to, about 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values. In certain embodiments, the volume of the sample includes, but is not limited to, about 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

F) Machine Learning

Details of the Network are described in detail in a variety of publications including International Application (IA) No. PCT/US2018/017504 filed Feb. 8, 2018, and PCT/US2018/057877 filed Oct. 26, 2018, each of which are hereby incorporated by reference herein for all purposes.

One aspect of the present invention provides a framework of machine learning and deep learning for analyte detection and localization. A machine learning algorithm is an algorithm that is able to learn from data. A more rigorous definition of machine learning is "A computer program is said to learn from experience E with respect to some class of tasks T and performance measure P, if its performance at tasks in T, as measured by P, improves with experience E." It explores the study and construction of algorithms that can learn from and make predictions on data—such algorithms overcome the static program instructions by making data driven predictions or decisions, through building a model from sample inputs.

Deep learning is a specific kind of machine learning based on a set of algorithms that attempt to model high level abstractions in data. In a simple case, there might be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

One aspect of the present invention is to provide two analyte detection and localization approaches. The first approach is a deep learning approach and the second approach is a combination of deep learning and computer vision approaches.

(i) Deep Learning Approach. In the first approach, the disclosed analyte detection and localization workflow consists of two stages, training and prediction. We describe training and prediction stages in the following paragraphs.

(a) Training Stage

In the training stage, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

The machine learning model receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" can refer to algorithms, systems and apparatus in the field of artificial intelligence that often use statistical techniques and artificial neural network trained from data without being explicitly programmed.

The annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In certain embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(b) Prediction Stage

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location and the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list. In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated only all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

Algorithm GlobalSearch (heatmap)
Input:
   heatmap
Output:
   loci
loci←{ }
sort(heatmap)
while (heatmap is not empty) {
   s←pop(heatmap)
   D←{disk center as s with radius R}
   heatmap=heatmap\D//remove D from the heatmap
   add s to loci
} After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, till the items are removed from the heatmap.

In the ordered list heatmap, each item has the knowledge of the proceeding item, and the following item. When removing an item from the ordered list, we make the following changes:

Assume the removing item is $x_r$, its proceeding item is $x_p$, and its following item is $x_f$.

For the proceeding item $x_p$, re-define its following item to the following item of the removing item. Thus, the following item of $x_p$ is now $x_f$.

For the removing item $x_1$, un-define its proceeding item and following item, which removes it from the ordered list.

For the following item $x_f$, re-define its proceeding item to the proceeding item of the removed item. Thus, the proceeding item of $x_f$ is now $x_p$.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the peak, we calculate the local area surrounding the peak but with smaller value. We remove this region from the heatmap and find the next peak from the remaining pixels. The process is repeated only all pixels are removed from the heatmap.

Algorithm LocalSearch (s, heatmap)
Input:
    s: starting location (x, y)
    heatmap
Output:
    s: location of local peak.
We only consider pixels of value>0.
Algorithm Cover (s, heatmap)
Input:
    s: location of local peak.
    heatmap:
Output:
    cover: a set of pixels covered by peak:

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

Algorithm Localization (heatmap)
Input:
    heatmap
Output:
    loci
loci←{ }
pixels←{all pixels from heatmap}
while pixels is not empty {
    s←any pixel from pixels
    s←LocalSearch(s, heatmap)//s is now local peak probe local region of radius R surrounding s for better local peak
    r←Cover(s, heatmap)
    pixels←pixels \r//remove all pixels in cover
    add s to loci (ii) Mixture of Deep Learning and Computer Vision Approaches. In the second approach, the detection and localization are realized by computer vision algorithms, and a classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

(a) Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

(b) Localization. After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

(c) Classification. The deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being a analyte.

G) Applications, Bio/Chemical Biomarkers, and Health Conditions

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In certain embodiments, the sample comprises a human body fluid. In certain embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In embodiments, the sample is at least one of a biological sample, an environmental sample, and a biochemical sample.

The devices, systems and the methods in the present invention find use in a variety of different applications in various fields, where determination of the presence or absence, and/or quantification of one or more analytes in a sample are desired. For example, the subject method finds use in the detection of proteins, peptides, nucleic acids, synthetic compounds, inorganic compounds, and the like. The various fields include, but not limited to, human, veterinary, agriculture, foods, environments, drug testing, and others.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present inventions of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

An implementation of the devices, systems and methods in the present invention can include a) obtaining a sample, b) applying the sample to CROF device containing a capture agent that binds to an analyte of interest, under conditions suitable for binding of the analyte in a sample to the capture agent, c) washing the CROF device, and d) reading the CROF device, thereby obtaining a measurement of the amount of the analyte in the sample. In certain embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the CROF device can be placed in a microfluidic device and the applying step b) can include applying a sample to a microfluidic device comprising the CROF device.

In any embodiment, the reading step d) can include detecting a fluorescence or luminescence signal from the CROF device.

In any embodiment, the reading step d) can include reading the CROF device with a handheld device configured to read the CROF device. The handheld device can be a mobile phone, e.g., a smart phone.

In any embodiment, the CROF device can include a labeling agent that can bind to an analyte-capture agent complex on the CROF device.

In any embodiment, the devices, systems and methods in the present invention can further include, between steps c) and d), the steps of applying to the CROF device a labeling agent that binds to an analyte-capture agent complex on the CROF device, and washing the CROF device.

In any embodiment, the reading step d) can include reading an identifier for the CROF device. The identifier can be an optical barcode, a radio frequency ID tag, or combinations thereof.

In any embodiment, the devices, systems and methods in the present invention can further include applying a control sample to a control CROF device containing a capture agent that binds to the analyte, wherein the control sample includes a known detectable amount of the analyte, and reading the control CROF device, thereby obtaining a control measurement for the known detectable amount of the analyte in a sample.

In any embodiment, the sample can be a diagnostic sample obtained from a subject, the analyte can be a biomarker, and the measured amount of the analyte in the sample can be diagnostic of a disease or a condition.

In any embodiment, the devices, systems and methods in the present invention can further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In any embodiment, the devices, systems and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the applying step b) can include isolating miRNA from the sample to generate an isolated miRNA sample, and applying the isolated miRNA sample to the disk-coupled dots-on-pillar antenna (CROF device) array.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the CROF device array can include a plurality of capture agents that each binds to an environmental marker, and wherein the reading step d) can include obtaining a measure of the amount of the plurality of environmental markers in the sample. In any embodiment, the sample can be a foodstuff sample, wherein the analyte can be a foodstuff marker, and wherein the amount of the foodstuff marker in the sample can correlate with safety of the foodstuff for consumption.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained. In any embodiment, the CROF device array can include a plurality of capture agents that each binds to a foodstuff marker, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the CROF device can be employed. Suitable methods can include using a pipet, dropper, syringe, etc. In certain embodiments, when the CROF device is located on a support in a dipstick format, as described below, the sample can be applied to the CROF device by dipping a sample-receiving area of the dipstick into the sample.

A sample can be collected at one time, or at a plurality of times. Samples collected over time can be aggregated and/or processed (by applying to a CROF device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the CROF device to remove unbound sample components can be done in any convenient manner, as described above. In certain embodiments, the surface of the CROF device is washed using binding buffer to remove unbound sample components. Detectable labeling of the analyte can be done by any convenient method. The analyte can be labeled directly or indirectly. In direct labeling, the analyte in the sample is labeled before the sample is applied to the CROF device. In indirect labeling, an unlabeled analyte in a sample is labeled after the sample is applied to the CROF device to capture the unlabeled analyte, as described below.

The samples from a subject, the health of a subject, and other applications of the present invention are further described below. Exemplary samples, health conditions, and application are also disclosed in, e.g., U.S. Pub. Nos. 2014/0154668 and 2014/0045209, which are hereby incorporated by reference.

The present inventions find use in a variety of applications, where such applications are generally analyte detection applications in which the presence of a particular analyte in a given sample is detected at least qualitatively, if not quantitatively. Protocols for carrying out analyte detection assays are well known to those of skill in the art and need not be described in great detail here. Generally, the sample suspected of comprising an analyte of interest is contacted with the surface of a subject nanosensor under conditions sufficient for the analyte to bind to its respective capture agent that is tethered to the sensor. The capture agent has highly specific affinity for the targeted molecules of interest. This affinity can be antigen-antibody reaction where antibodies bind to specific epitope on the antigen, or a DNA/RNA or DNA/RNA hybridization reaction that is sequence-specific between two or more complementary strands of nucleic acids. Thus, if the analyte of interest is present in the sample, it likely binds to the sensor at the site of the capture agent and a complex is formed on the sensor surface. Namely, the captured analytes are immobilized at the sensor surface. After removing the unbounded analytes, the presence of this binding complex on the surface of the sensor (e.g. the immobilized analytes of interest) is then detected, e.g., using a labeled secondary capture agent.

Specific analyte detection applications of interest include hybridization assays in which the nucleic acid capture agents are employed and protein binding assays in which polypeptides, e.g., antibodies, are employed. In these assays, a sample is first prepared and following sample preparation, the sample is contacted with a subject nanosensor under specific binding conditions, whereby complexes are formed between target nucleic acids or polypeptides (or other molecules) that are complementary to capture agents attached to the sensor surface.

In one embodiment, the capture oligonucleotide is synthesized single strand DNA of 20-100 bases length, that is thiolated at one end. These molecules are immobilized on the nanodevices' surface to capture the targeted single-strand DNA (which can be at least 50 bp length) that has a sequence that is complementary to the immobilized capture DNA. After the hybridization reaction, a detection single strand DNA (which can be of 20-100 bp in length) whose sequence are complementary to the targeted DNA's unoccupied nucleic acid is added to hybridize with the target. The detection DNA has its one end conjugated to a fluorescence label, whose emission wavelength are within the plasmonic resonance of the nanodevice. Therefore by detecting the fluorescence emission emanate from the nanodevices' surface, the targeted single strand DNA can be accurately detected and quantified. The length for capture and detection DNA determine the melting temperature (nucleotide strands will separate above melting temperature), the extent of misparing (the longer the strand, the lower the misparing).

One of the concerns of choosing the length for complementary binding depends on the needs to minimize misparing while keeping the melting temperature as high as possible. In addition, the total length of the hybridization length is determined in order to achieve optimum signal amplification.

A subject sensor can be employed in a method of diagnosing a disease or condition, comprising: (a) obtaining a liquid sample from a patient suspected of having the disease or condition, (b) contacting the sample with a subject nanosensor, wherein the capture agent of the nanosensor specifically binds to a biomarker for the disease and wherein the contacting is done under conditions suitable for specific binding of the biomarker with the capture agent; (c) removing any biomarker that is not bound to the capture agent; and (d) reading a light signal from biomarker that remain bound to the nanosensor, wherein a light signal indicates that the patient has the disease or condition, wherein the method further comprises labeling the biomarker with a light-emitting label, either prior to or after it is bound to the capture agent. As will be described in greater detail below, the patient can suspected of having cancer and the antibody binds to a cancer biomarker. In other embodiments, the patient is suspected of having a neurological disorder and the antibody binds to a biomarker for the neurological disorder.

The applications of the subject sensor include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In certain embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

In some cases, the nanosensor can be employed to detect a biomarker that is present at a low concentration. For example, the nanosensor can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

The following table provides a list of protein biomarkers that can be detected using the subject nanosensor (when used in conjunction with an appropriate monoclonal antibody), and their associated diseases. One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva.

H) Utility

The subject method finds use in a variety of different applications where determination of the presence or absence, and/or quantification of one or more analytes in a sample are desired. For example, the subject method finds use in the detection of proteins, peptides, nucleic acids, synthetic compounds, inorganic compounds, and the like.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present invention of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

I) Diagnostic Method

In certain embodiments, the subject method finds use in detecting biomarkers. In certain embodiments, the devices, systems and methods in the present invention of using CROF are used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. Thus, the sample, e.g. a diagnostic sample, can include various fluid or solid samples.

In some instances, the sample can be a bodily fluid sample from a subject who is to be diagnosed. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate and/or other excretions. The samples can include nasopharyngeal wash. Nasal swabs, throat swabs, stool samples, hair, finger nail, ear wax, breath, and other solid, semi-solid, or gaseous samples can be processed in an extraction buffer, e.g., for a fixed or variable amount of time, prior to their analysis. The extraction buffer or an aliquot thereof can then be processed similarly to other fluid samples if desired. Examples of tissue samples of the subject can include but are not limited to, connective tissue, muscle tissue, nervous tissue, epithelial tissue, cartilage, cancerous sample, or bone.

In some instances, the subject from which a diagnostic sample is obtained can be a healthy individual, or can be an individual at least suspected of having a disease or a health condition. In some instances, the subject can be a patient.

In certain embodiments, the CROF device includes a capture agent configured to specifically bind a biomarker in a sample provided by the subject. In certain embodiments, the biomarker can be a protein. In certain embodiments, the biomarker protein is specifically bound by an antibody capture agent present in the CROF device. In certain embodiments, the biomarker is an antibody specifically bound by an antigen capture agent present in the CROF device. In certain embodiments, the biomarker is a nucleic acid specifically bound by a nucleic acid capture agent that is complementary to one or both strands of a double-stranded nucleic acid biomarker, or complementary to a single-stranded biomarker. In certain embodiments, the biomarker is a nucleic acid specifically bound by a nucleic acid binding protein. In certain embodiments, the biomarker is specifically bound by an aptamer.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers can influence the choices of drug treatment or administration regimes given to an individual. In evaluating potential drug therapies, a biomarker can be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject method. Furthermore, the early detection of biomarkers associated with diseases is facilitated by the high sensitivity of the devices, systems and methods in the present invention, as described above. Due to the capability of detecting multiple biomarkers with a mobile device, such as a smartphone, combined with sensitivity, scalability, and ease of use, the presently disclosed method finds use in portable and point-of-care or near-patient molecular diagnostics.

In certain embodiments, the subject method finds use in detecting biomarkers for a disease or disease state. In certain instances, the subject method finds use in detecting biomarkers for the characterization of cell signaling pathways and intracellular communication for drug discovery and vaccine development. For example, the subject method can be used to detect and/or quantify the amount of biomarkers in diseased, healthy or benign samples. In certain embodiments, the subject method finds use in detecting biomarkers for an infectious disease or disease state. In some cases, the biomarkers can be molecular biomarkers, such as but not limited to proteins, nucleic acids, carbohydrates, small molecules, and the like.

The subject method find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

In certain embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

Other pathogens that can be detected in a diagnostic sample using the devices, systems and methods in the present invention include, but are not limited to: *Varicella zoster, Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*, etc.

In some cases, the CROF device can be employed to detect a biomarker that is present at a low concentration. For example, the CROF device can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva. It will also be clear to one with ordinary skill in the art that the subject CROF devices can be configured to capture and detect many more biomarkers known in the art that are diagnostic of a disease or health condition.

A biomarker can be a protein or a nucleic acid (e.g., mRNA) biomarker, unless specified otherwise. The diagnosis can be associated with an increase or a decrease in the level of a biomarker in the sample, unless specified otherwise. Lists of biomarkers, the diseases that they can be used to diagnose, and the sample in which the biomarkers can be detected are described in Tables 1 and 2 of U.S. provisional application Ser. No. 62/234,538, filed on Sep. 29, 2015, which application is incorporated by reference herein.

In some instances, the devices, systems and methods in the present invention is used to inform the subject from whom the sample is derived about a health condition thereof. Health conditions that can be diagnosed or measured by the devices, systems and methods in the present invention, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. Table 3 of U.S. provisional application Ser. No. 62/234,538, filed on Sep. 29, 2015, which application is incorporated by reference herein, provides a list of biomarker that can be detected using the present CROF device (when used in conjunction with an appropriate monoclonal antibody, nucleic acid, or other capture agent), and their associated health conditions.

J) Kits

Aspects of the present disclosure include a kit that find use in performing the devices, systems and methods in the present invention, as described above. In certain embodiments, the kit includes instructions for practicing the subject methods using a hand held device, e.g., a mobile phone. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that can be present is a website address which can be used via the Internet to access the information at a removed site. The kit can further include a software for implementing a method for measuring an analyte on a device, as described herein, provided on a computer readable medium. Any convenient means can be present in the kits.

In certain embodiments, the kit includes a detection agent that includes a detectable label, e.g. a fluorescently labeled antibody or oligonucleotide that binds specifically to an analyte of interest, for use in labeling the analyte of interest. The detection agent can be provided in a separate container as the CROF device, or can be provided in the CROF device. In certain embodiments, the kit includes a control sample that includes a known detectable amount of an analyte that is to be detected in the sample. The control sample can be provided in a container, and can be in solution at a known concentration, or can be provided in dry form, e.g., lyophilized or freeze dried. The kit can also include buffers for use in dissolving the control sample, if it is provided in dry form.

EXAMPLES

A) Example 1

An OAC is a QMAX device having two plates.

The first plate is a rectangle shaped PMMA plate with a flat surface and a thickness in the range of 0.8 mm to 1.1 mm, 0.5 mm to 1.5 mm, or 0.3 mm to 2 mm; a length in the range of 28 mm to 32 mm, 25 mm to 35 mm, or 20 mm to 50 mm; and a width in the range of 20 mm to 28 mm, 15 mm to 34 mm, or 10 mm to 40 mm.

The second plate is a rectangle shaped PMMA film with a flat surface and an array of micro pillar array imprinted on the flat surface. The PMMA film has a thickness in the range of 0.8 mm to 1.1 mm, 0.5 mm to 1.5 mm, or 0.3 mm to 2 mm; a length in the range of 28 mm to 32 mm, 25 mm to 35 mm, or 20 mm to 50 mm; and a width in the range of 20 mm to 28 mm, 15 mm to 34 mm, or 10 mm to 40 mm. In some embodiments, when putting the first plate and the second plate together to hold sample, at least three sides of the second plate is inside the area of the first plate. The pillar array has a shape of either rectangle or square, a flat top, and a pillar lateral size in the range of 30 um to 40 um, 25 um to 45 um, 20, um to 50 um, 10 um to 60 um, or 5 um to 70 um, a pillar height in the range of 10 um to 30 um, 5 um to 40 um, 1 um to 50 um, or 0.1 um to 100 um, and a distance between two neighboring pillar center in a range of 80 to 110 um, 60 to 130 um, or 30 to 180 um, or 30 to 200 um.

B) Hemoglobin Measurements Using OAC—Using One Wavelength

In an experiment of the present invention, an OAC is a QMAX device has two plates. The first plate is 1 mm thick flat PMMA substrate with a size of 30 mm×24 mm. The second plate is 175 um thick PMMA film with a micro pillar array on it with a size of 24 mm×22 mm. The pillar array has pillar size of 30 um×40 um, pillar to pillar edge distance of 80 um, and pillar height of 10 um or 30 um.

The sample is a fresh whole blood (2.5 uL for 10 um pillar height, 5 uL for 30 um pillar height), which was dropped in a location of the first plate, and pressed by the second plate.

Figure 5:
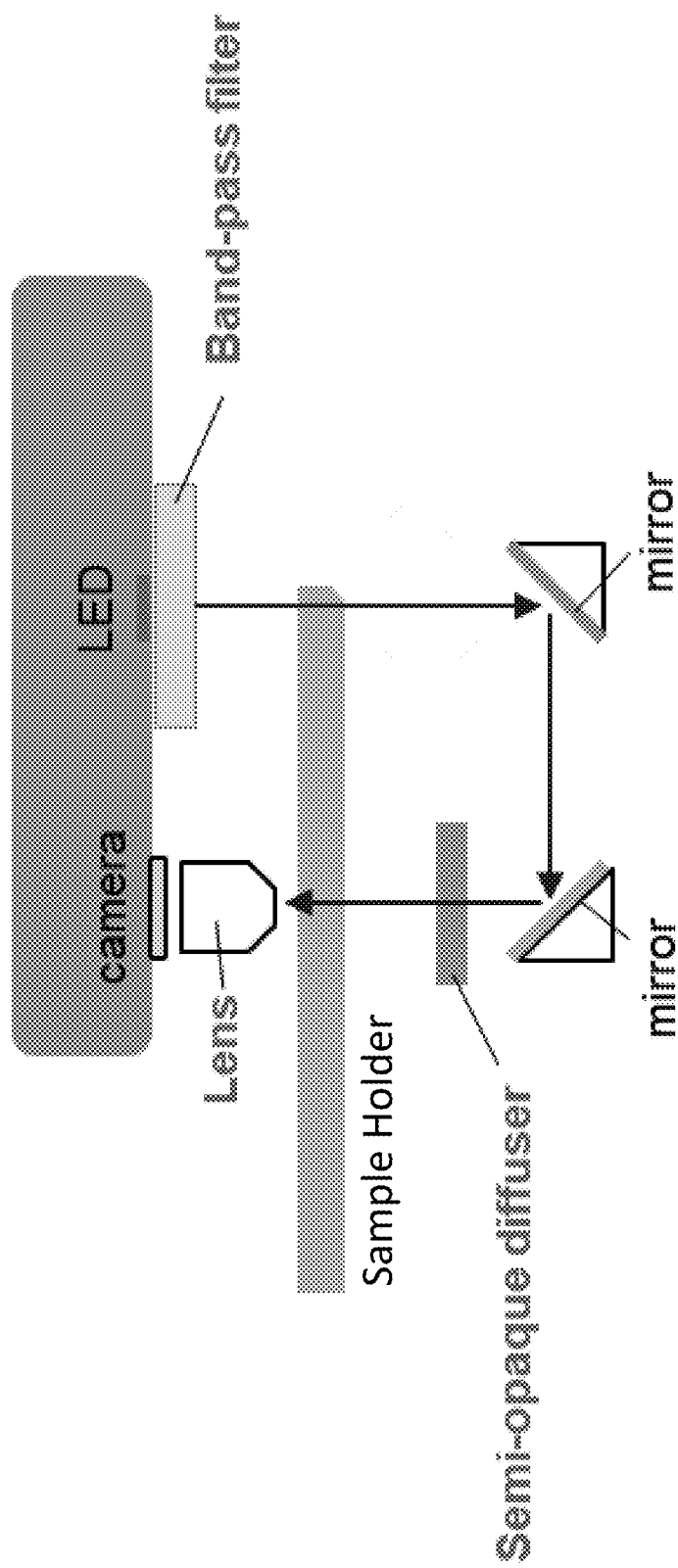
FIG. 5 illustrates an optical setup for measuring hemoglobin in QMAX card.

In the optical measurements, as shown in FIG. 5, LED light are filtered by a band pass filter (532 nm to 576 nm) and illuminates onto two 45 degree mirror sets. The light then goes through a semi-opaque diffuser, to eliminate coherence of the point source's wavefront and ensure the intensity change is only due to the absorption. Finally, the light transmits the QMAX device and is collected by a lens and camera.

The LED light and camera used here can be both from a phone.

The picture taken by camera shows that there are 2 regions. One region is the pillar region, the other is the blood region.

The absorption of light in pillar region is neglectable. Also, the extinction coefficient of oxygenated hemoglobin [HbO2] and deoxygenated hemoglobin [Hb] in wavelength range of 532 nm to 576 nm is similar $\varepsilon_{Hb} \approx \varepsilon_{HbO_2} = 44000\text{-}48000 \text{ cm}^{-1}/M$.

Thus, $$OD^{green} = \ln(I/Io) = \varepsilon_{HbO_2}^{green}\{[Hb] + [HbO_2]\}L$$

Figure 6:
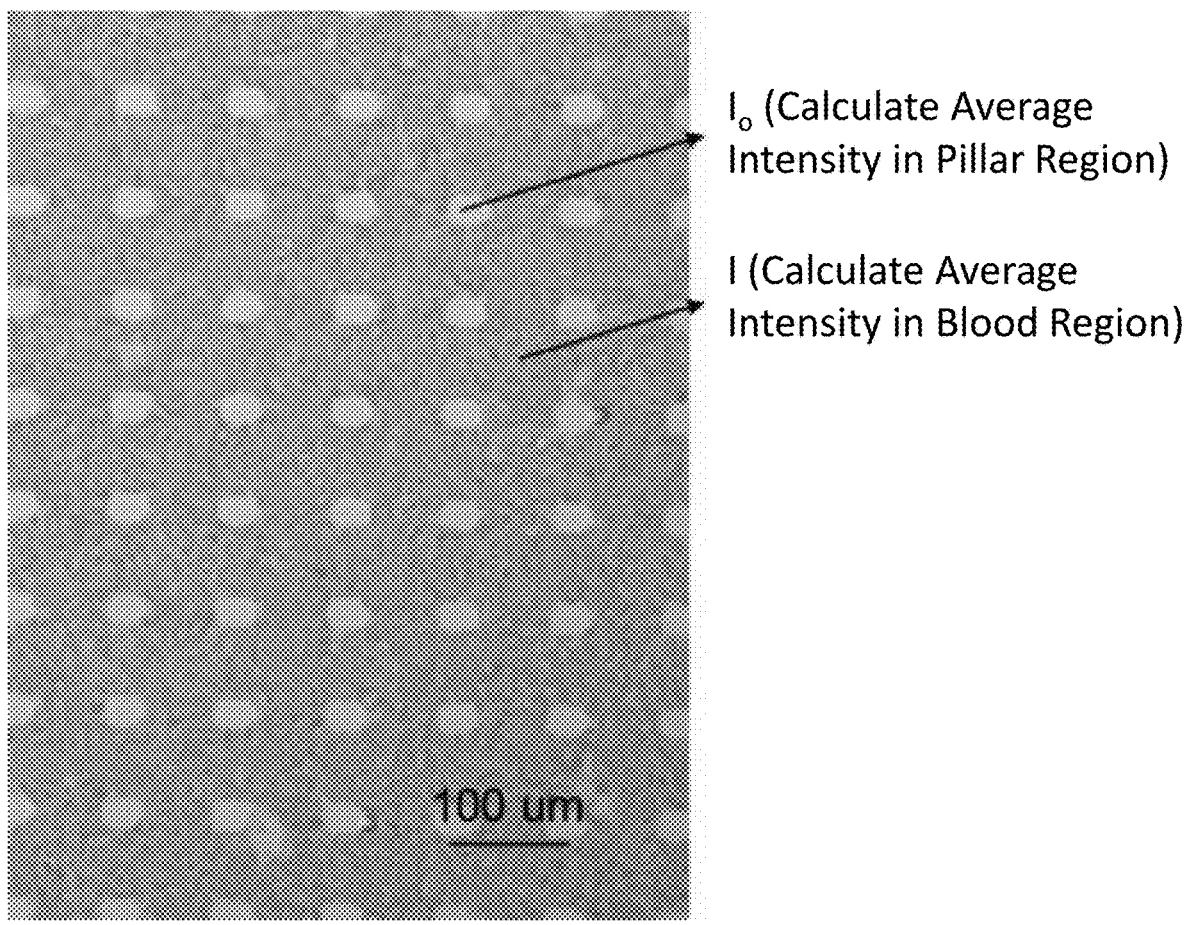
FIG. 6 illustrates an exemplary hemoglobin measurement in a QMAX card taken by an iPhone.

As shown in FIG. 6, I is the average intensity in the blood region, Io is the average intensity in the center of the pillar region. When calculating the average intensity, we subtract 5 um area near the pillar boundary to reduce the analyze error.

$$\text{Total hemoglobin concentration} = [HbO_2] + [Hb] = \frac{\ln\left(\frac{I}{Io}\right)}{\varepsilon \times gap}$$

Figure 7:
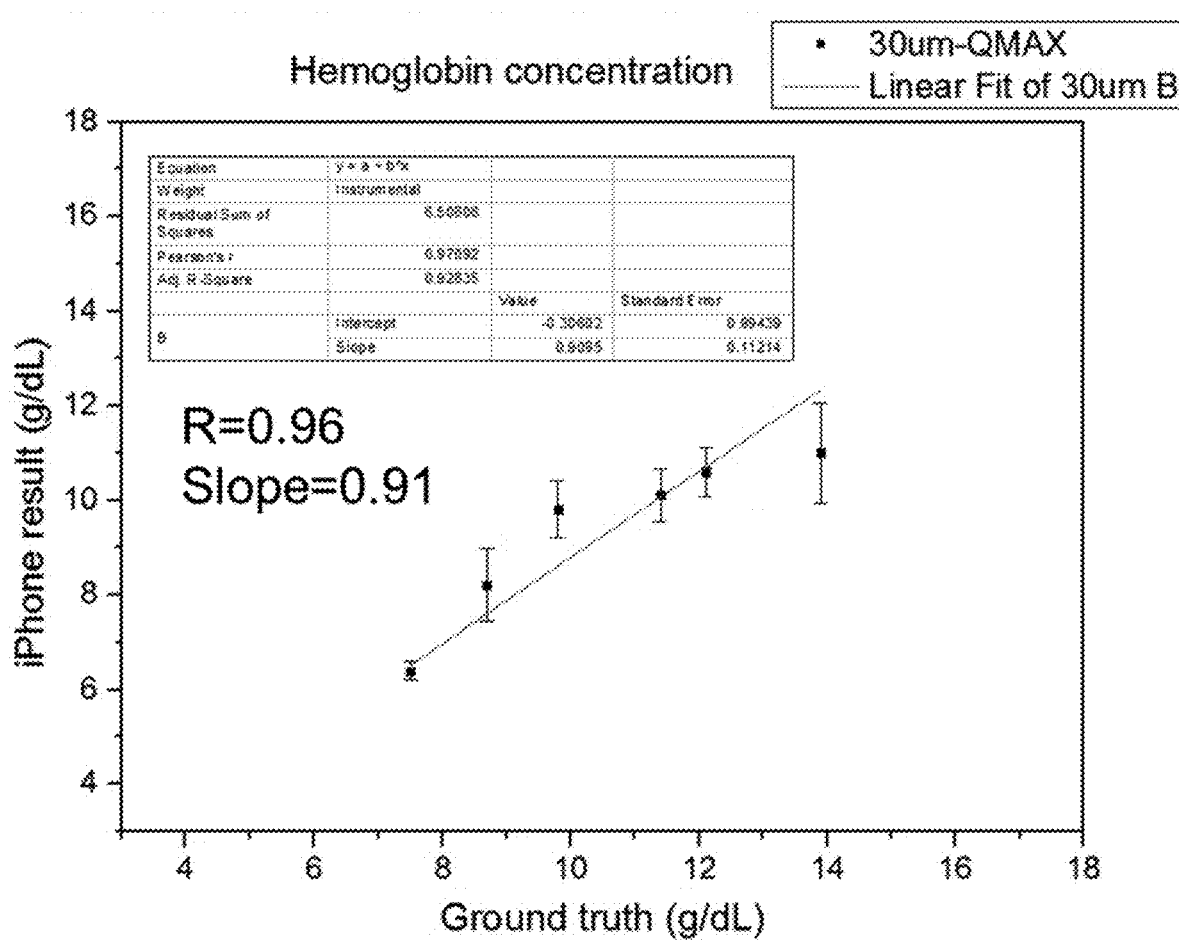
FIG. 7 illustrates an exemplary QMAX hemoglobin measurement compared with the gold standard (Abbott Emerald Hemocytometer).

We measured the hemoglobin in blood ranging from 6 g/dL to 11 g/dL with both QMAX device setup and commercial Abbott Emerald hemocytometer machine and compared the results as shown in Figure. 7. For each concentration, we measured 3 cards to calculate the standard deviation.

From the results, the repeatability (CV) of hemoglobin measurements by QMAX card for same blood is around 5% and the R2 value compared with gold standard is 96%.

C) Example-3

Figure 8:
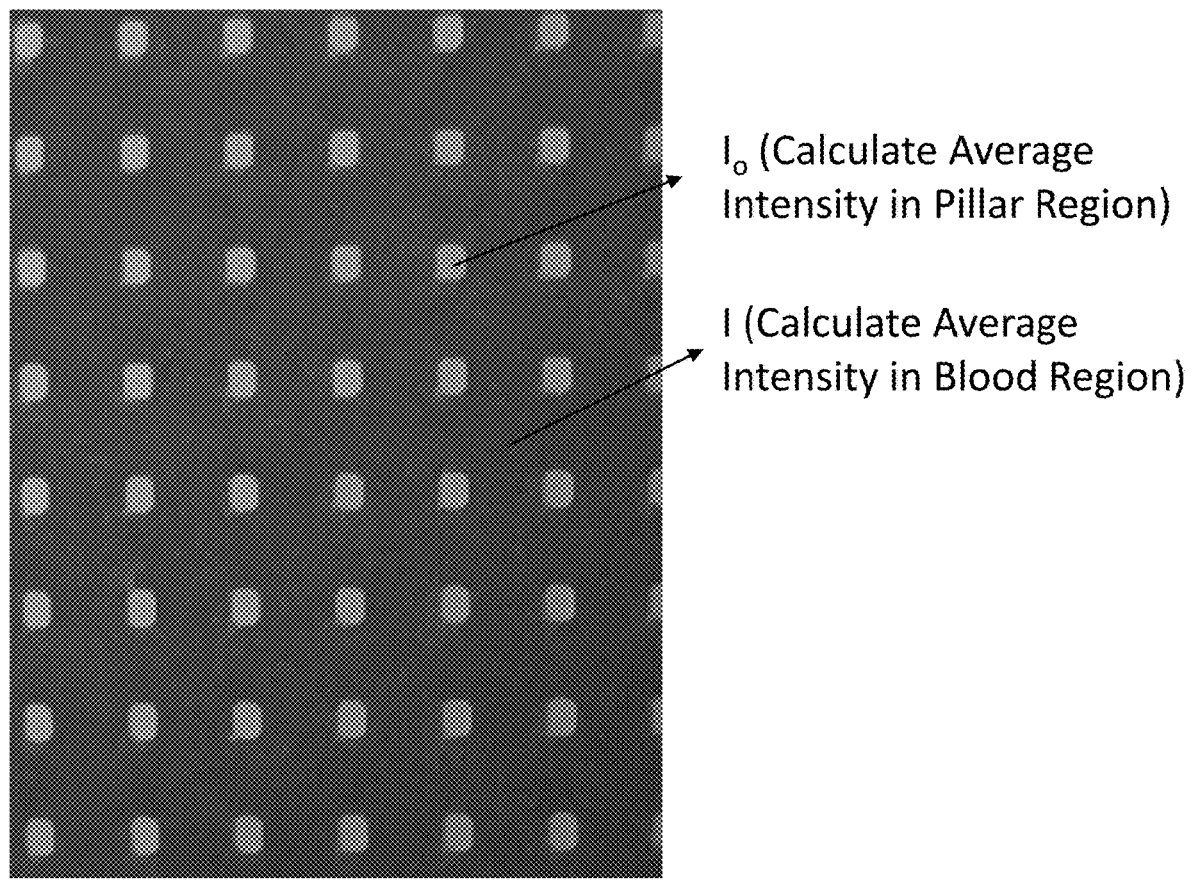
FIG. 8 illustrates an exemplary hemoglobin measurement in a QMAX card taken by iPhone.

FIG. 8. illustrates an example of a hemoglobin measurement, where the image of an optical transmission image through a thin layer of whole blood (without lysing) in an OAC (e.g. the sample holder described in FIG. 1), and the light source is a diffusive light source (e.g. a light diffusion is placed in front of a point light source), and the image taken by an iPhone. In FIG. 8, the light-guiding spacers are periodically placed on a QMAX card, with a vertical periodic distance of 120 um and a horizontal periodic distance of 110 um.

Figure 9:
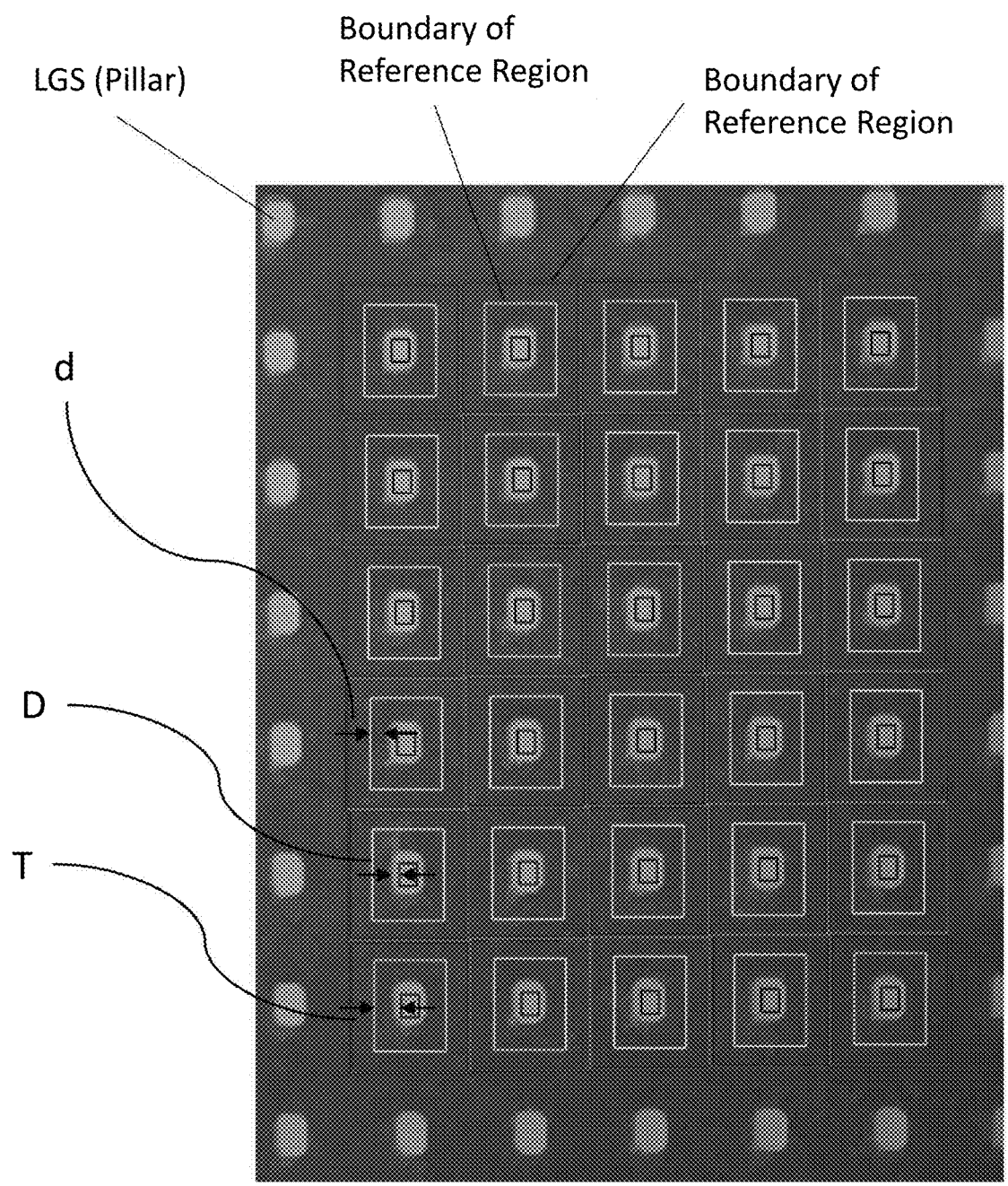
FIG. 9 illustrates an exemplary method for selecting sampling regions and reference regions.

FIG. 9 illustrates an example of the sample regions and reference regions selected for determining hemoglobin using the image from FIG. 8. The boundary of the sampling regions and the reference are marked.

In FIG. 9, the reference regions (with outer boundaries colored in blue) are inside light-guiding spacers; D, the distance between the edges of the reference region and the light-guiding spacer, is 10 urn; d, the distance between the edges of the sampling region and the light-guiding spacer, is 30 urn; and T, the distance between the edges of the sampling region and the reference region, is 40 urn.

D) Image Processing

According to the present invention, the image processing algorithm on hemoglobin absorption measurement consists of the following steps:
1. Light-guiding spacer detection
2. Reference region and sampling region determination
3. Individual region calculation
4. Polling The light-guiding spacer detection is to detect and locate light-guiding spacers, which are periodically placed on a QMAX card. Various object detection algorithm can be employed, including, but not limited to, template matching, blob detection, contour detection, etc. The detection can be performance in a single color channel in a color space (RGB, HSV, HSI, Lab, YCrCb, etc.), such as the green channel in a RGB color space, or the hue channel in the HSV space, or a combination of two or more color channels, such as using red-green-blue channels in a RGB color space, etc.

After the periodic light-guiding spaces are detected and located, the reference regions (which are inside the light-guiding spacers) and sampling regions are selected. The sizes of reference regions and sampling regions, and the distance among the edges of the light-guiding spaces, reference regions, and sampling regions are disclosed in the invention.

For reference regions and sampling regions, they can be associated by the relative location and distance. When one (or more) reference region is associated with one (or more) sampling region, a hemoglobin absorption measurement can be calculated by the method disclosed in the invention. One embodiment is to associate one reference region with the sampling region with the shortest distance, and calculate the hemoglobin absorption measurement for each association.

A pooling algorithm is to pool hemoglobin absorption measurements from each associate and produce a single hemoglobin absorption measurement. Various pooling algorithm can be utilized, such as median, mean, max, min, k-means, etc.

In some embodiments, the imaging processing uses artificial intelligence and/or machine learning. In some embodiments, the imaging processing uses deep learning.

E) Using Two Wavelengths

Similar to above experimental setup, except using 2 different band pass filters and taking 2 pictures.

After taking the picture, by calculating the OD=ln (I/Io) of blood with two different wavelength $\lambda_1$ and $\lambda_2$, e.g, 660 nm and 940 nm:

$$OD^{\lambda_1} = \{\varepsilon_{Hb}^{\lambda_1}[Hb] + \varepsilon_{HbO_2}^{\lambda_1}[HbO_2]\}L$$

$$OD^{\lambda_2} = \{\varepsilon_{Hb}^{\lambda_2}[Hb] + \varepsilon_{HbO_2}^{\lambda_2}[HbO_2]\}L$$

We get:

$$[HbO_2] = \frac{\varepsilon_{Hb}^{\lambda_2} OD^{\lambda_1} - \varepsilon_{Hb}^{\lambda_1} OD^{\lambda_2}}{L(\varepsilon_{Hb}^{\lambda_2}\varepsilon_{HbO_2}^{\lambda_1} - \varepsilon_{Hb}^{\lambda_1}\varepsilon_{HbO_2}^{\lambda_2})}$$

$$[Hb] = \frac{\varepsilon_{HbO_2}^{\lambda_2} OD^{\lambda_1} - \varepsilon_{HbO_2}^{\lambda_1} OD^{\lambda_2}}{L(\varepsilon_{Hb}^{\lambda_1}\varepsilon_{HbO_2}^{\lambda_2} - \varepsilon_{Hb}^{\lambda_2}\varepsilon_{HbO_2}^{\lambda_1})}$$

$\varepsilon$ is the extinction coefficient of hemoglobin, [Hb] and [HbO$_2$] is the concentration of hemoglobin, and L is the length of light path through the sample or the gap size of QMAX device.

Thus, total hemoglobin concentration=[HbO$_2$]+[Hb].

This method could further provide the detailed information of the ratio between [HbO2] and [Hb].

F) Light Guiding Spacer, Sampling Region, and Reference Region

In some embodiments, the sampling region boundary has a size of 120 um by 110 um; the edge of sampling area has a size of 60 um by 45 um; the light guiding spacer or pillar has a size of 40 um by 30 um; the reference region has a size of 20 um by 15 um. In some embodiments, the area of reference region is 1/2 of the size of the light guiding spacer area, the distance between edge of the sampling area and that of the light guiding spacer is 1/2 of the light guiding spacer area, and the area of the sampling area is equal to the periodic inter spacer distance.

1. The method or device of any prior claim, wherein the spacers have pillar shape and nearly uniform cross-section.
2. The method or device of any prior claim, wherein the inter spacer distance (SD) is equal or less than about 150 um (micrometer).
3. The method or device of any prior claim, wherein the inter spacer distance (SD) is equal or less than about 100 urn (micrometer).
4. The method or device of any prior claim, wherein the fourth power of the inter-spacer-distance (ISD) divided by the thickness (h) and the Young's modulus (E) of the flexible plate (ISD$^4$/(hE)) is 5×10$^6$ um$^3$/GPa or less.
5. The method or device of any prior claim, wherein the fourth power of the inter-spacer-distance (ISD) divided by the thickness (h) and the Young's modulus (E) of the flexible plate (ISD$^4$/(hE)) is 5×10$^5$ um$^3$/GPa or less.
6. The method or device of any prior claim, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).
7. The method or device of any prior claim, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5\times10^6$ $um^3/GPa$ or less.
8. The device of any prior device claim, wherein the ratio of the inter-spacing distance of the spacers to the average width of the spacer is 2 or larger, and the filling factor of the spacers multiplied by the Young's modulus of the spacers is 2 MPa or larger.
9. The method or device of any prior claim, wherein the analytes is the analyte in 5 detection of proteins, peptides, nucleic acids, synthetic compounds, and inorganic compounds.
10. The method or device of any prior claim, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.
11. The method or device of any prior claim, wherein the spacers have a shape of pillars and a ratio of the width to the height of the pillar is equal or larger than one.
12. The method of any prior claim, wherein the sample that is deposited on one or both of the plates has an unknown volume.
13. The method or device of any prior claim, wherein the spacers have a shape of pillar, and the pillar has substantially uniform cross-section.
14. The method or device of any prior claim, wherein the samples is for the detection, purification and quantification of chemical compounds or biomolecules that correlates with the stage of certain diseases.
15. The method or device of any prior claim, wherein the samples is related to infectious and parasitic disease, injuries, cardiovascular disease, cancer, mental disorders, neuropsychiatric disorders, pulmonary diseases, renal diseases, and other and organic diseases.
16. The method or device of any prior claim, wherein the samples is related to the detection, purification and quantification of microorganism.
17. The method or device of any prior claim, wherein the samples is related to virus, fungus and bacteria from environment, e.g., water, soil, or biological samples.
18. The method or device of any prior claim, wherein the samples is related to the detection, quantification of chemical compounds or biological samples that pose hazard to food safety or national security, e.g. toxic waste, anthrax.
19. The method or device of any prior claim, wherein the samples is related to quantification of vital parameters in medical or physiological monitor.
20. The method or device of any prior claim, wherein the samples is related to glucose, blood, oxygen level, total blood count.
21. The method or device of any prior claim, wherein the samples is related to the detection and quantification of specific DNA or RNA from biosamples.
22. The method or device of any prior claim, wherein the samples is related to the sequencing and comparing of genetic sequences in DNA in the chromosomes and mitochondria for genome analysis.
23. The method or device of any prior claim, wherein the samples is related to detect reaction products, e.g., during synthesis or purification of pharmaceuticals.
24. The method or device of any prior claim, wherein the samples is cells, tissues, bodily fluids, and stool.
25. The method or device of any prior claim, wherein the sample is the sample in the detection of proteins, peptides, nucleic acids, synthetic compounds, inorganic compounds.
26. The method or device of any prior claim, wherein the sample is the sample in the fields of human, veterinary, agriculture, foods, environments, and drug testing.

The method or device of any prior claim, wherein the sample is a biological sample is selected from blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epit Other Descriptions and Additional Examples of Present Inventions The present invention comprises further a combination of the disclosures above together a variety of embodiments that are given in the below, which can be combined in multiple ways as long as the various components do not contradict one another. The embodiments should be regarded as a single invention file: each filing has other filing as the references and is referenced in its entirety and for all purpose, rather than as a discrete independent. These embodiments include not only the disclosures in the current file, but the documents that are herein referenced, incorporated, or to which priority is claimed.

A device for analyzing an analyte in a sample using optical transmission, comprising: a first plate, a second plate, and light-guiding spacers (LGS's), wherein:

the first plate and second plate are movable relative to each other into different configurations, including an open configuration and a closed configuration;

each of the plates comprises an inner surface that has a sample contact area for contacting a sample that contains or is suspected to contain analyte; and each of the light-guiding spacers has a pillar shape, has bottom end fixed on one of the plate and the top end having flat surface, wherein the light-guiding spacers have a uniform height of 300 um (microns) or less, wherein, in a closed configuration, the top end flat surface is in direct contact with the plate, and the cross-section of each light-guiding spacer is larger than the wavelength of the light that analyzes the sample, wherein at least one of the light-guiding spacer is inside the sample;

wherein the open configuration is a configuration, the two plates are separated apart, the spacing between the plates is not regulated by the light-guiding spacers, and the sample is deposited on one or both of the plates;

wherein the closed configuration is a configuration, which is configured after the sample deposition in the open configuration; at least part of the sample is compressed by the two plates into a layer of uniform thickness, wherein the uniform thickness of the layer is confined by the t plates and is regulated by the plates and the light-guiding spacers; and A device for analyzing an analyte in a sample using optical transmission, comprising:

a first plate, a second plate, a light guiding spacer (LGS) or more, a sampling region, and a reference region, wherein:

the first plate and second plate are configured to sandwich a sample, this is for an optical transmission analysis by light, into a thin layer between the plates, and each plate has a sample contact area on its inner surface that contacts the sample;

each of the light-guiding spacer (LGS) or more LGS's has a pillar shape, is sandwiched between the two plates with each end of the pillar in direct contact to one of the plates forming a LGS-plate contact area, and is configured to allow the light transmits from the first plate, through the LGS, to the second plate without going through a sample, the sampling region is the region that the light can go through, in sequence, the first plate, the sample, and the second plate, wherein the sampling region does not have the LGS; and the reference region is the region that the light transmits through, in sequence, the first plate, the light-guiding spacer, and the second plate, without going through the sample;

wherein the LGS-contact areas and a lateral cross-section of the LGS are larger than the wavelength of the light, wherein the light-guiding spacer is surrounded by or near the sample; and wherein the sample in the sampling region has a thickness of 300 um or less.

LGSs are an periodic array

LGSs are an periodic array and the period is 500 urn or less.

LGSs are an periodic array and the period is 250 urn or less.

LGSs are an periodic array and the period is 150 urn or less.

the height is 60 urn or less the height is 40 urn or less.

in the closed configuration: (a) at least one spacer in the sample contact area has its top surface in direct contact with one of the plates, and the at least one spacer and the regions of the plates above and below the at least one spacer define a reference region wherein the reference region is transparent to light within a wavelength range, and (b) at least one region in the sample contact area on one plate and its corresponding region on the other plate are not occupied by the light-guiding spacers, defining a sampling region that is transparent to light within the same wavelength range.

A device for analyzing an analyte in a sample using optical transmission, comprising:

a first plate, a second plate, and a light-guiding spacer, wherein:

the first plate and second plate are configured to hold a sample that contains or is suspected to contain an analyte, wherein at least part the sample is between the two plates and is in contact with both plates; and the light-guiding spacer has a pillar shape and a predetermined substantially height, wherein the light-guiding spacer is surrounded by the sample during an optical transmission measurement;

wherein top and bottom surfaces of the light-guiding spacers are substantially flat and the top and bottom surfaces of the light guiding spacer is in direct contact with the plates, wherein the area of the top and bottom surfaces and average lateral cross-section of each spacer is respectively larger than the wavelength of the light that analyze the sample, and wherein: (a) the at least one spacer and the regions of the plates directly above and below the at least one spacer define a reference region that is transparent to light within a wavelength range and passing through the plates and the spacer, and (b) at least one region in the sample contact area on one plate and its corresponding region on the other plate are not occupied by the light-guiding spacers, defining a sampling region that is transparent to light within the same wavelength range.

A device for analyzing an analyte in a sample, comprising:

a first plate, a second plate, and light-guiding spacers, wherein:

the first plate and second plate are movable relative to each other into different configurations, including an open configuration and a closed configuration;

each of the plates comprises an inner surface that has a sample contact area for contacting a sample that contains or is suspected to contain an analyte; and the light-guiding spacers have a pillar shape and a predetermined substantially uniform height, wherein top and bottom surfaces of the light-guiding spacers are substantially flat and the bottom surface is fixed on the inner surface of one or the plates, wherein the area of the top and bottom surfaces and average lateral cross-section of each spacer is respectively larger than 1 the wavelength of the light that analyze the sample, wherein at least one of the light-guiding spacers is inside the sample contact area;

wherein the open configuration is a configuration, in which: the two plates are separated apart, the spacing between the plates is not regulated by the light-guiding spacers, and the sample is deposited on one or both of the plates;

wherein the closed configuration is a configuration, which is configured after the sample deposition in the open configuration; and in the closed configuration: at least part of the sample is compressed by the two plates into a layer of highly uniform thickness, wherein the uniform thickness of the layer is confined by the sample contact areas of the plates and is regulated by the plates and the light-guiding spacers; and wherein in the closed configuration, (a) at least one spacer in the sample contact area has its top surface in direct contact with one of the plates, and the at least one spacer and the regions of the plates above and below the at least one spacer define a reference region wherein the reference region is transparent to light within a wavelength range, and (b) at least one region in the sample contact area on one plate and its corresponding region on the other plate are not occupied by the light-guiding spacers, defining a sampling region that is transparent to the light within the wavelength range.

A device for analyzing tin a sample, comprising:
a first plate, a second plate, and a light guiding spacer, wherein:
the first plate and second plate are configured to sandwich a sample into a thin layer;
a first plate, a second plate, and a light guiding spacer, wherein:
the first plate and second plate are configured to sandwich a sample into a thin layer;
the light-guiding spacer has a pillar shape that is sandwiched between the two plates, wherein each end of the pillar directly contact one of the plates so that there is no sample between the end of the pillar and the respective plate, wherein the light-guiding spacer is either surrounded by or near the sample, and wherein the direct-contact area and an average lateral cross-section of the pillar is respectively at least 1 um^2 (square micron) or larger;
wherein the spacing between the inner surfaces of the plates is 200 um or less.

An apparatus for sample analysis using optical transmission, comprising:
a device of any of prior device embodiments, a light source, a camera; and an adaptor, wherein
the light source is configured to emit light in the wavelength range that is configured to go through the reference region;
the camera is configured to image the reference region and the sampling region.
the adaptor is configured to position the device, the light source, and the camera relative to each other, so that the light from the light source goes through the reference region and the sampling region and is imaged by the camera.

The apparatus of any prior apparatus embodiments, further comprising:
a processor, which is configured to process the images captured by the camera, and determine a property of the analyte in the sample based on comparing light transmissions from the reference region and the sampling region.

The apparatus of any prior claim, wherein the camera and the processor are parts of a single mobile device.

The apparatus of any prior claim, wherein the light source and the processor are parts of a single mobile device.

The apparatus of any prior claim, wherein the light source, the camera, and the processor are parts of a single mobile device.

The apparatus of any prior apparatus embodiments, wherein the mobile device is a smart phone.

A method for sample analysis using an transmitted light, comprising the steps of: having a device of any prior device embodiments;
depositing the sample at the open configuration of the device, wherein the sample is suspected of containing an analyte;
bringing the device into the closed configuration;
having a light source that has a wavelength that is configured to go through the reference region of the device;
having an imager that is configured to image the reference region and the sampling region of the device;
having an adaptor that is configured to position the device, the light source, and the camera relative to each other, so that the light from the light source goes through the reference region and the sampling region and is imaged by the camera;
determining a property of the analyte by comparing the light transmission from the sampling region and the reference region.

The device, method, or system of any prior claim, wherein the analyte is hemoglobin.

The device, method, or system of any prior claim, wherein the analyte is type of cells.

Add all analytes.

Add different applications.

Add key distances between the light transmission.

The device, method, or system of any prior claim, wherein the thickness of the sample layer is regulated by plates and the light-guiding spacers and is substantially the same as the uniform height of the light-guiding spacers;

The device, method, or system of any prior claim, wherein the analyte is red blood cells.

The device, method, or system of any prior claim, wherein the analyte is white blood cells.

The device, method, or system of any prior claim, wherein the reference region and the sampling region have a same size.

The device, method, or system of any prior claim, wherein the reference region is within a corresponding area of the cross section of the light-guide spacer.

The device, method, or system of any prior claim, wherein the reference region is less than 0.1 um^2, less than 0.2 um^2, less than 0.5 um^2, less than 1 um^2, less than 2 um^2, less than 5 um^2, less than 10 um^2, less than 20 um^2, less than 50 um^2, less than 100 um^2, less than 200 um^2, less than 500 um^2, less than 1000 um^2, less than 2000 um^2, less than 5000 um^2, less than 10000 um^2, less than 20000 um^2, less than 50000 um^2, less than 100000 um^2, less than 200000 um^2, less than 500000 um^2, less than 1 mm^2, less than 2 mm^2, less than 5 mm^2, less than 10 mm^2, less than 20 mm^2, or less than 50 mm^2, or in a range between any of the two values.

The device, method, or system of any prior claim, wherein the device further comprises a plurality of light guiding spacers that have substantially uniform height, and wherein at least one of the light-guiding spacers is inside the sample contact area.

The device, method, or system of any prior claim, wherein the device further comprises a plurality of light guiding spacers that have substantially uniform height, wherein the distance between two neighboring light guiding spacers are known, and wherein at least one of the light-guiding spacers is inside the sample contact area.

The device, method, or system of any prior claim, wherein the device further comprises a plurality of light guiding spacers that have substantially uniform height, wherein the distances between two neighboring light guiding spacers are known and are substantially constant (i.e. the light guiding spacers are substantially a periodic array), and wherein at least one of the light-guiding spacers is inside the sample contact area.

The device, method, or system of any prior claim, wherein the bottom surface of the light guiding spacer is fixed on the inner surface of one of the plates by molding the light guiding spacer on the inner surface of the plate.

The device, method, or system of any prior claim, wherein the bottom surface of the light guiding spacer is fixed on the inner surface of one of the plates and is made of the same material as the inner surface.

The device, method, or system of any prior claim, wherein the bottom surface of the light guiding spacer is fixed on the inner surface of one of the plates, and is made of the same material as the inner surface, and the bottom surface of the light guiding spacer has no interface with on the inner surface of the plate.

The device, method, or system of any prior claim, wherein the wavelength of the light is longer than 300 nm, and wherein the wavelength of the light is also less than 20 μm, less than 15 μm, less than 10 μm, less than 5 μm, less than 4 μm, less than 3 μm, less than 2 μm, less than 1 μm, less than 800 nm, less than 750 nm, less than 700 nm, less than 650 nm, less than 600 nm, less than 550 nm, less than 500 nm, less than 450 nm, less than 400 nm, or in a range between any of the two values.

The device, method, or system of any prior claim, wherein the wavelength of the light is longer than 500 nm, and wherein the wavelength of the light is also less than 600 nm, less than 590 nm, less than 580 nm, less than 570 nm, less than 560 nm, less than 550 nm, less than 540 nm, less than 530 nm, less than 520 nm, less than 510 nm, or in a range between any of the two values.

The device, method, or system of any prior claim, wherein the average lateral cross-section of each light-guiding spacer is less than 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, 500,000 um^2, 1 mm^2, 2 mm^2, 5 mm^2, 10 mm^2, 50 mm^2, or in a range between any of the two values.

The device, method, or system of any prior claim, wherein the average lateral cross-section of each light-guiding spacer is less than 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, or in a range between any of the two values.

The device, method, or system of any prior claim, wherein the average lateral cross-section of each light-guiding spacer is less than 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, or in a range between any of the two values.

The device, method, or system of any prior claim, wherein the sample contact area is larger than 100 um^2(micron-square), larger than 200 um^2, larger than 400 um^2, larger than 600 um^2, larger than 800 um^2, larger than 1,000 um^2, larger than 2,000 um^2, larger than 4,000 um^2, larger than 6,000 um^2, larger than 8,000 um^2, larger than 10,000 um^2, larger than 20,000 um^2, larger than 40,000 um^2, larger than 60,000 um^2, larger than 80,000 um^2, larger than 100,000 um^2, larger than 200,000 um^2, larger than 250,000 um^2, larger than 500,000 um^2(micron-square), or in a range between any of the two values.

The device, method, or system of any prior claim, wherein a predetermined constant inter-spacer distance that is at least about 2 times larger than the size of the analyte.

The device, method, or system of any prior claim, wherein a predetermined constant inter-spacer distance that is larger than the size of the analyte by a factor that is at least 2 times, at least 6 times, at least 8 times, at least 10 times, at least 20 times, at least 40 times, at least 60 times, at least 80 times, or at least 100 times.

The device, apparatus, or method of any prior claim, wherein the analyte is a biomarker, an environmental marker, or a foodstuff marker.

The device, apparatus, or method of any prior claim, wherein the analyte is a biomarker indicative of the presence or severity of a disease or condition.

The device, apparatus, or method of any prior claim, wherein the analyte is a cell, a protein, or a nucleic acid.

The device, apparatus, or method of any prior claim, wherein the analyte is hemoglobin.

The device, apparatus, or method of any prior claim, wherein the analyte comprises proteins, peptides, nucleic acids, synthetic compounds, inorganic compounds, organic compounds, bacteria, virus, cells, tissues, nanoparticles, and other molecules, compounds, mixtures and substances thereof.

The device, apparatus, or method of any prior claim, wherein the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

The device, apparatus, or method of any prior claim, wherein the sample is original, diluted, or processed forms of blood.

The device, apparatus, or method of any prior claim, wherein the sample comprises whole blood.

The device, apparatus, or method of any prior claim, wherein the sample comprises an aggregation agent that induces aggregation of the interference elements.

The device, apparatus, or method of any prior claim, wherein the sample holder comprises wells that configured to hold the sample.

The device, apparatus, or method of any prior claim, wherein the sample holder comprises a first plate, and a second plate, and spacers.

The device, apparatus, or method of any prior claim, wherein the sample holder comprises a first plate, a second plate, and spacers, wherein the spacers are configured to regulate a gap between the plates when the plates are pressed against each, compressing the sample into a thin layer.

The device, apparatus, or method of any prior claim, wherein the sample holder comprises a first plate, a second plate, and spacers, and wherein:
  the plates are moveable relative to each other into different configurations, including an open configuration and a closed configuration;
  in the open configuration: the two plates are separated apart, the spacing between the plates is not regulated by the spacers, and the sample is deposited on one or both of the plates; and
  in the closed configuration, which is configured after the sample deposition in the open configuration: at least part of the sample is compressed by the two plates into a layer of highly uniform thickness and is substantially stagnant relative to the plates, wherein the uniform thickness of the layer is regulated by the plates and the spacers.

The device, apparatus, or method of any prior claim, wherein the sample holder comprises a Q-card, which comprises a first plate, a second plate, and spacers, wherein the spacers are configured to regulate a gap between the plates when the plates are pressed against each, compressing the sample into a thin layer.

The device, apparatus, or method of any prior claim, wherein the sample holder comprises a first plate, a second plate, and spacers, wherein the spacers have a uniform height and a constant inter-spacer distance; and
  ii. the sample is compressed by the sample holder into a thin layer with a uniform thickness that is regulated by the height of the spacers.

The device, apparatus, or method of any prior claim, wherein the sample is compressed into a layer of uniform thickness that substantially equals uniform height of spacers that are fixed to one or both of the plates.

The apparatus, kit or method of any prior claim, wherein the sample is compressed into a layer of uniform thickness that has a variation of less than 15%, 10%, 5%, 2%, 1%, or in a range between any of the two values.

The device, apparatus, or method of any prior claim, wherein the sample, when compressed, has a thickness of 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values.

The device, apparatus, or method of any prior claim, wherein the sample holder comprises a first plate and a second plate, wherein each of the plate has a thickness of 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, or in a range between any two of these values.

The device, apparatus, or method of any prior claim, wherein at least part of the sample is compressed into a thin layer that has an average thickness of 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 um or less, 0.2 um or less, 0.1 um or less, 50 nm or less, 20 nm or less, 10 nm or less, or in a range between any of the two values.

The device, apparatus, or method of any prior claim, wherein at least part of the sample is compressed into a thin layer, and wherein for a specific part of the sample that has an average thickness of 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 um or less, 0.2 um or less, 0.1 um or less, 50 nm or less, 20 nm or less, 10 nm or less, or in a range between any of the two values, only the interference rich regions exist.

The device, apparatus, or method of any prior claim, wherein at least part of the sample is compressed into a thin layer, wherein for a specific part of the sample that has an average thickness of 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 um or less, 0.2 um or less, 0.1 um or less, 50 nm or less, 20 nm or less, 10 nm or less, or in a range between any of the two values, only the interference poor regions exist.

The device, apparatus, or method of any prior claim, wherein at least part of the sample is compressed into a thin layer that has an average thickness of in a range of 0.5-2 um, 0.5-3 um, 0.5-5 um, 0.5-10 um, 0.5-20 um, 0.5-30 um, or 0.5-50 um.

The device, apparatus, or method of any prior claim, wherein at least part of the sample is compressed into a thin layer that has an average thickness of 500 um or less.

The device, apparatus, or method of any prior claim, wherein at least part of the sample is compressed into a thin layer that has an average thickness of 200 um or less.

The device, apparatus, or method of any prior claim, wherein at least part of the sample is compressed into a thin layer that has an average thickness of 100 um or less.

The device, apparatus, or method of any prior claim, wherein at least part of the sample is compressed into a thin layer that has an average thickness of 50 um or less.

The device, apparatus, or method of any prior claim, wherein at least part of the sample is compressed into a thin layer that has an average thickness of 25 um or less.

The device, apparatus, or method of any prior claim, wherein at least part of the sample is compressed into a thin layer that has an average thickness of 10 um or less.

The device, apparatus, or method of any prior claim, wherein at least part of the sample is compressed into a thin layer that has an average thickness of 5 um or less.

The device, apparatus, or method of any prior claim, wherein at least part of the sample is compressed into a thin layer that has an average thickness of 3 um or less.

The device, apparatus, or method of any prior claim, wherein at least part of the sample is compressed into a thin layer that has an average thickness of 2 um or less.

The device, apparatus, or method of any prior claim, wherein at least part of the sample is compressed into a thin layer that has an average thickness of 1 um or less.

The device, apparatus, or method of any prior claim, wherein at least part of the sample is compressed into a thin layer that has an average thickness of 500 nm or less.

The device, apparatus, or method of any prior claim, wherein at least part of the sample is compressed into a thin layer that has an average thickness of 100 nm or less.

The device, apparatus, or method of any prior claim, wherein at least part of the sample is compressed into a thin layer that has an average thickness in the range of 0.5-2 um, 0.5-3 um, or 0.5-5 um.

The device, apparatus, or method of any prior claim, wherein the average thickness of the layer of uniform thickness is in the range of 2 um to 2.2 um and the sample is blood.

The device, apparatus, or method of any prior claim, wherein the average thickness of the layer of uniform thickness is in the range of 2.2 um to 2.6 um and the sample is blood.

The device, apparatus, or method of any prior claim, wherein the average thickness of the layer of uniform thickness is in the range of 1.8 um to 2 um and the sample is blood.

The device, apparatus, or method of any prior claim, wherein the average thickness of the layer of uniform thickness is in the range of 2.6 um to 3.8 um and the sample is blood.

The device, apparatus, or method of any prior claim, wherein the average thickness of the layer of uniform thickness is in the range of 1.8 um to 3.8 um and the sample is whole blood without a dilution by another liquid.

The device, apparatus, or method of any prior claim, wherein the average thickness of the layer of uniform thickness is about equal to a minimum dimension of an analyte in the sample.

The device, apparatus, or method of any prior claim, wherein the final sample thickness device is configured to analyze the sample in 300 seconds or less.

The device, apparatus, or method of any prior claim, wherein the final sample thickness device is configured to analyze the sample in 180 seconds or less.

The device, apparatus, or method of any prior claim, wherein the final sample thickness device is configured to analyze the sample in 60 seconds or less.

The device, apparatus, or method of any prior claim, wherein the final sample thickness device is configured to analyze the sample in 30 seconds or less.

The device, apparatus, or method of any prior claim, wherein the imager comprises a camera.

The device, apparatus, or method of any prior claim, wherein the imager is a part of the detector.

The device, apparatus, or method of any prior claim, wherein the imager is the entirety of the detector.

The device, apparatus, or method of any prior claim, wherein the imager is directed by the software to capture one or more images of the sample, identify the interference element regions and the interference element free regions, and digitally separate the interference element regions from the interference element free regions.

The device, apparatus, or method of any prior claim, wherein the imager comprises a filter that is configured to filter signals from the sample.

The device, apparatus, or method of any prior claim, wherein the imager comprises a light source that is configured to illuminate the sample.

The device, apparatus, or method of any prior claim, wherein the apparatus or method are used for detection of proteins, peptides, nucleic acids, synthetic compounds, inorganic compounds, organic compounds, bacteria, virus, cells, tissues, nanoparticles, and other molecules, compounds, mixtures and substances thereof.

The device, apparatus, or method of any prior claim, wherein the apparatus or method are used for diagnostics, management, and/or prevention of human diseases and conditions.

The device, apparatus, or method of any prior claim, wherein the apparatus or method are used for diagnostics, management, and/or prevention of veterinary diseases and conditions, or for diagnostics, management, and/or prevention of plant diseases and conditions.

The device, apparatus, or method of any prior claim, wherein the apparatus or method are used for environments testing and decontamination.

The device, apparatus, or method of any prior claim, wherein the apparatus or method are used for agricultural or veterinary applications.

The device, apparatus, or method of any prior claim, wherein the apparatus or method are used for food testing.

The device, apparatus, or method of any prior claim, wherein the apparatus or method are used for drug testing and prevention.

The device, apparatus, or method of any prior claim, wherein the apparatus or method are used for detecting and/or measuring an analyte in blood.

The device, apparatus, or method of any prior claim, wherein the apparatus or method are used for a colorimetric assay.

The device, apparatus, or method of any prior claim, wherein the apparatus or method are used for a fluorescence assay.

The device, apparatus, or method of any prior claim, wherein the plates are movable relative to each.

The device, apparatus, or method of any prior claim, wherein the spacers are fixed on one or both of the plates and have a uniform height.

The device, apparatus, or method of any prior claim, wherein the first plate and second plate are configured to compress the sample into a layer of uniform thickness that substantially equals the height of the spacers.

The device, apparatus, or method of any prior claim, wherein the spacers have a uniform height of 1 mm or less, 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 um or less, 0.2 um or less, 0.1 um or less, 50 nm or less, 20 nm or less, 10 nm or less, or in a range between any of the two values.

The device, apparatus, or method of any prior claim, wherein the spacers have a uniform height in the range of 0.5-2 um, 0.5-3 um, 0.5-5 um, 0.5-10 um, 0.5-20 um, 0.5-30 um, or 0.5-50 um.

The device, apparatus, or method of any prior claim, wherein at least one of the plates has a thickness of 100 mm or less, 50 mm or less, 25 mm or less, 10 mm or less, 5 mm or less, 1 mm or less, 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 urn or less, 2 urn or less, 1.8 urn or less, 1.5 urn or less, 1 urn or less, 0.5 urn or less, 0.2 urn or less, or 0.1 urn or less, or in a range between any of the two values.

The device, apparatus, or method of any prior claim, wherein at least one of the plates has a thickness in the range of 0.5 to 1.5 mm; around 1 mm; in the range of 0.15 to 0.2 mm; or around 0.175 mm.

The device, apparatus, or method of any prior claim, wherein at least one of the plates has a lateral area of 1 $mm^2$ or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, 500 $cm^2$ or less, 1000 $cm^2$ or less, 5000 $cm^2$ or less, 10,000 $cm^2$ or less, 10,000 $cm^2$ or less, or in a range between any two of these values The device, apparatus, or method of any prior claim, wherein at least one of the plates has a lateral area of in the range of 500 to 1000 $mm^2$; or around 750 $mm^2$ The device, apparatus, or method of any prior claim, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

The device, apparatus, or method of any prior claim, wherein the thickness of the flexible plate times the Young's modulus of the flexible plate is in the range 60 to 750 GPa-urn.

The device, apparatus, or method of any prior claim, wherein for a flexible plate, the fourth power of the interspacer-distance (ISD) divided by the thickness of the flexible plate (h) and the Young's modulus (E) of the flexible plate, $ISD^4/(hE)$, is equal to or less than $10^6$ um$^3$/GPa.

The device, apparatus, or method of any prior claim, wherein one or both plates comprises a location marker, either on a surface of or inside the plate, that provide information of a location of the plate.

The device, apparatus, or method of any prior claim, wherein one or both plates comprises a scale marker, either on a surface of or inside the plate, that provide information of a lateral dimension of a structure of the sample and/or the plate.

The device, apparatus, or method of any prior claim, wherein one or both plates comprises an image marker, either on a surface of or inside the plate, that assists an imaging of the sample.

The device, apparatus, or method of any prior claim, wherein the inter-spacer distance is in the range of 7 urn to 120 urn.

The device, apparatus, or method of any prior claim, wherein the inter-spacer distance is in the range of 120 urn to 200 urn.

The device, apparatus, or method of any prior claim, wherein the spacers are pillars with a cross-sectional shape selected from round, polygonal, circular, square, rectangular, oval, elliptical, or any combination of the same.

The device, apparatus, or method of any prior claim, wherein the spacers have a pillar shape and have a substantially flat top surface, wherein, for each spacer, the ratio of the lateral dimension of the spacer to its height is at least 1.

The device, apparatus, or method of any prior claim, wherein each spacer has the ratio of the lateral dimension of the spacer to its height is at least 1.

The device, apparatus, or method of any prior claim, wherein the minimum lateral dimension of spacer is less than or substantially equal to the minimum dimension of an analyte in the sample.

The device, apparatus, or method of any prior claim, wherein the minimum lateral dimension of spacer is in the range of 0.5 um to 100 um.

The device, apparatus, or method of any prior claim, wherein the minimum lateral dimension of spacer is in the range of 0.5 um to 10 um.

The device, apparatus, or method of any prior claim, wherein the spacers have a pillar shape, and the sidewall corners of the spacers have a round shape with a radius of curvature at least 1 μm.

The device, apparatus, or method of any prior claim, wherein the spacers have a density of at least 100/mm$^2$.

The device, apparatus, or method of any prior claim, wherein the spacers have a density of at least 1000/mm$^2$.

The device, apparatus, or method of any prior claim, wherein at least one of the plates is transparent The device, apparatus, or method of any prior claim, wherein at least one of the plates is made from a flexible polymer.

The device, apparatus, or method of any prior claim, wherein, for a pressure that compresses the plates, the spacers are not compressible and/or, independently, only one of the plates is flexible.

The device, apparatus, or method of any prior claim, wherein the flexible plate has a thickness in the range of 10 um to 200 um.

The device, apparatus, or method of any prior claim, wherein the variation of sample thickness is less than 30%.

The device, apparatus, or method of any prior claim, wherein the variation of sample thickness is less than 10%.

The device, apparatus, or method of any prior claim, wherein the variation of sample thickness is less than 5%.

The device, apparatus, or method of any prior claim, wherein the first and second plates are connected and are configured to be changed from the open configuration to the closed configuration by folding the plates.

The device, apparatus, or method of any prior claim, wherein the first and second plates are connected by a hinge and are configured to be changed from the open configuration to the closed configuration by folding the plates along the hinge.

The device, apparatus, or method of any prior claim, wherein the first and second plates are connected by a hinge that is a separate material to the plates, and are configured to be changed from the open configuration to the closed configuration by folding the plates along the hinge.

The device, apparatus, or method of any prior claim, wherein the first and second plates are made in a single piece of material and are configured to be changed from the open configuration to the closed configuration by folding the plates.

The device, apparatus, or method of any prior claim, wherein the layer of uniform thickness sample is uniform over a lateral area that is at least 1 mm$^2$.

The device, apparatus, or method of any prior claim, wherein the spacers are fixed on a plate by directly embossing the plate or injection molding of the plate.

The device, apparatus, or method of any prior claim, wherein the materials of the plate and the spacers are selected from polystyrene, PMMA, PC, COC, COP, or another plastic.

The device, method, or system of any prior claim, wherein the first plate further comprises a scattering surface on an inner surface thereof.

The device, method, or system of any prior claim, wherein the first plate is substantially transparent.

The device, method, or system of any prior claim, wherein the first plate has a reflectivity in a range from 1% to 80%.

The device, method, or system of any prior claim, wherein the first plate has a reflectivity in a range that is larger than 1%, 2%, 4%, 8%, 10%, 20%, 30%, 40%, 50%, 60%, 70%, or 80%, or in a range between any of the two values.

The device, method, or system of any prior claim, wherein the first plate is made from PMMA.

The device, method, or system of any prior claim, wherein the second plate has a reflectivity in a range from 1% to 100%.

The device, method, or system of any prior claim, wherein the second plate has a reflectivity in a range that is larger than 1%, 2%, 4%, 8%, 10%, 20%, 30%, 40%, 50%, 60%, 70%, 80%, 90%, or 95%, or in a range between any of the two values.

The device, method, or system of any prior claim, wherein at least a part of the inner surface and the outer surface of the first plate is substantially flat.

The device, method, or system of any prior claim, wherein the scattering surface has a reflectivity larger than 90% over the entire spectrum of the illuminating light for illuminating the sample.

The device, method, or system of any prior claim, wherein the scattering surface has a reflectivity larger than 50%, 60%, 70%, 80%, 90%, or in a range between any of the two values.

The device, method, or system of any prior claim, wherein the scattering surface is coated with a metal film.

The device, method, or system of any prior claim, wherein the scattering surface is coated with a metal film and the metal film has a thickness thereof in a range from 10 nm to 100 nm.

The device, method, or system of any prior claim, wherein the scattering surface is coated with a metal film and the thickness of the metal film is less than 10 nm, 15 nm, 20 nm, 25 nm, 30 nm, 40 nm, 50 nm, 60 nm, 80 nm, or 100 nm, or in a range between any of the two values.

The device, method, or system of any prior claim, wherein the scattering surface is coated with a metal film and the metal film includes one or more of aluminum film, silver film, and gold film.

The device, method, or system of any prior claim, the scattering surface has a transmissibility in a range from 10% to 30%.

The device, method, or system of any prior claim, the scattering surface has a transmissibility that is less than 10%, 15%, 20%, 25%, or 30%, or in a range between any of the two values.

The device, method, or system of any prior claim, wherein the one plate of the first and second plates and the scattering surface of the other plate enhances the light trapping.

The device, method, or system of any prior claim, wherein the scattering surface has a reflectance that is dominated by Lambertian reflectance in the at least one wavelength range.

The device of, method, or system of any prior claim, wherein the scattering surface has a Lambertian reflectance that is larger than 0.8 in the at least one wavelength range.

The device, method, or system of any prior claim, wherein the scattering surface is a surface formed by chemical etching.

The device, method, or system of any prior claim, wherein the scattering surface is a surface formed by nanoimprint lithography.

The device, method, or system of any prior claim, wherein the scattering surface covers substantially all of the sample contact area of the first plate.

The device, method, or system of any prior claim, wherein the scattering surface covers a fraction of the sample contact area of the first plate.

The device, method, or system of any prior claim, wherein the part of the first plate is substantially transparent covers substantially all of the sample contact area of the second plate.

The device, method, or system of any prior claim, wherein the part of the first plate is substantially transparent covers a fraction of the sample contact area of the second plate.

The device, method, or system of any prior claim, wherein the scattering surface comprises a bumpy and wavy roughly surface.

The device, method, or system of any prior claim, wherein the scattering surface comprises a periodic texture.

The device, method, or system of any prior claim, wherein the scattering surface comprises an aperiodic texture.

The device, method, or system of any prior claim, wherein the scattering surface has an average roughness in a range between 2 µm to 5 µm.

The device, method, or system of any prior claim, wherein the scattering surface has an average roughness that is less than 2.0 µm, 2.5 µm, 3.0 µm, 3.5 µm, 4.0 µm, 4.5 µm, or 5.0 µm, or in a range between any of the two values.

The device, method, or system of any prior claim, wherein the light-guiding spacers are fixed to the inner surface of the first plate and have a predetermined uniform height.

The device, method, or system of any prior claim, wherein the adapter comprises:
 an adaptor housing that has an exit aperture for positioning an imager;
 a passive illuminator; and
 wherein the passive illuminator is on the adaptor and is positioned around the outside peripheral of exit aperture.

The device, method, or system of any prior claim, wherein the adaptor housing is configured to reduce ambient light outside the adaptor housing entering into inside adaptor housing.

The device, method, or system of any prior claim, wherein the adaptor comprises one or two light-guides each having an end thereof aligned with the entrance aperture of the optics chamber to cause light entering such end of the light-guide to travel through the light-guide to reach a corresponding end of the passive illuminator.

The device, apparatus, or method of any prior claim, wherein one or more light-guides and the passive illuminator are jointly formed by an optical fiber.

The device, apparatus, or method of any prior claim, wherein the passive illuminator is in the form of ring configured to surround an optical axis of a lens in the camera of the smartphone when the apparatus is engaged with the smartphone.

The device, apparatus, or method of any prior claim, wherein the apparatus further comprises an auxiliary lens having an optical axis thereof aligned with the optical axis of the lens in the camera of the smartphone when the apparatus is engaged with the smartphone.

The device, apparatus, or method of any prior claim, wherein the apparatus further comprises an auxiliary lens having a diameter that is at least 2 mm, 3 mm, 4 mm, 5 mm, 10 mm, 15 mm, 20 mm, 25 mm, 30 mm, 40 mm, or 50 mm, or in a range between any of the two values.

The device, apparatus, or method of any prior claim, wherein the apparatus further comprises an optical condenser configured to be placed in front of the light source of the smartphone when the apparatus is engaged with the smartphone.

The device, apparatus, or method of any prior claim, wherein the diffuser comprises a volume diffusive material.

The device, apparatus, or method of any prior claim, wherein the diffuser comprises at least one textured surface.

The device, apparatus, or method of any prior claim, wherein the diffuser comprises a diffusive plate that is substantially uniform in thickness.

The device, apparatus, or method of any prior claim, wherein the diffuser comprises a diffusive plate including an area that has thickness that is larger than an average thickness of the diffusive plate.

The device, apparatus, or method of any prior claim, further comprising a reflector configured to reflect light emitted from the passive illuminator towards the diffuser.

The device, apparatus, or method of any prior claim, wherein the passive illuminator is formed by a side illumination fiber.

The device, apparatus, or method of any prior claim, wherein the passive illuminator is rotationally symmetric.

The device, apparatus, or method of any prior claim, wherein the passive illuminator is in the form of a circle.

The device, apparatus, or method of any prior claim, wherein the passive illuminator is in the form of a circle having a diameter thereof in a range between 5 mm and 100 mm.

The device, apparatus, or method of any prior claim, wherein the passive illuminator is in the form of a circle having a diameter that is at least 5 mm, 10 mm, 15 mm, 20 mm, 25 mm, 30 mm, 40 mm, 50 mm, 60 mm, 80 mm, or 100 mm, or in a range between any of the two values.

The device, apparatus, or method of any prior claim, wherein the passive illuminator is in the form of a convex polygon.

The device, apparatus, or method of any prior claim, wherein the passive illuminator is in the form of a star polygon.

The device, apparatus, or method of any prior claim, wherein the optical axis of the lens passes through a center of the passive illuminator.

The device, apparatus, or method of any prior claim, wherein the passive illuminator is rotationally non-symmetric.

The device, apparatus, or method of any prior claim, wherein the passive illuminator is in the form of an ellipse.

The device, apparatus, or method of any prior claim, wherein the passive illuminator has a substantially uniform cross-section.

The device, apparatus, or method of any prior claim, wherein all of the cross-sections at locations on more than 50% length of the passive illuminator are substantially identical in shape.

The device, apparatus, or method of any prior claim, wherein the shapes of substantially all of the cross-sections are in the form of a circle.

The device, apparatus, or method of any prior claim, wherein the shapes of substantially all the cross-sections are in the form of a circle having a diameter thereof in a range between 1.0 mm and 3.0 mm.

The device, apparatus, or method of any prior claim, wherein the shapes of substantially all of the cross-sections are in the form of a circle having a diameter that is at least 0.5 mm, 1.0 mm, 1.5 mm, 2.0 mm, 2.5 mm, 3 mm, 4 mm, 5 mm, 6 mm, 8 mm, or 10 mm, or in a range between any of the two values.

The device, apparatus, or method of any prior claim, wherein the shapes of substantially all of the cross-sections are in the form of an ellipse.

The device, apparatus, or method of any prior claim, wherein at least a segment of the side wall of the passive illuminator is formed by a diffusive surface.

The device, method, or system of any prior claim, wherein the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

The device, method, or system of any prior claim, wherein the sample is original, diluted, or processed forms of blood.

The device, method, or system of any prior claim, wherein the sample comprises whole blood.

The device, method, or system of any prior claim, wherein the sample is a biological sample, a chemical sample, an environmental sample, or a foodstuff sample.

The device, method, or system of any prior claim, wherein the analyte is a biomarker, an environmental marker, or a foodstuff marker.

The device, method, or system of any prior claim, wherein the analyte is a biomarker indicative of the presence or severity of a disease or condition.

The device, method, or system of any prior claim, wherein the analyte is a cell, a protein, or a nucleic acid.

The device, method, or system of any prior claim, wherein the analyte comprises proteins, peptides, nucleic acids, synthetic compounds, inorganic compounds, organic compounds, bacteria, virus, cells, tissues, nanoparticles, and other molecules, compounds, mixtures and substances thereof.

The device, method, or system of any prior claim, wherein the sample holder comprises wells that configured to hold the sample.

The device, method, or system of any prior claim, wherein the sample holder comprises a first plate, and a second plate, and spacers.

The device, method, or system of any prior claim, wherein the sample holder comprises a first plate, a second plate, and spacers, wherein the spacers are configured to regulate a gap between the plates when the plates are pressed against each, compressing the sample into a thin layer.

The device, method, or system of any prior claim, wherein the sample holder comprises a first plate, a second plate, and spacers, and wherein:
the plates are moveable relative to each other into different configurations, including an open configuration and a closed configuration;
in the open configuration: the two plates are separated apart, the spacing between the plates is not regulated by the spacers, and the sample is deposited on one or both of the plates; and
in the closed configuration, which is configured after the sample deposition in the open configuration: at least part of the sample is compressed by the two plates into a layer of highly uniform thickness and is substantially stagnant relative to the plates, wherein the uniform thickness of the layer is regulated by the plates and the spacers.

The device, method, or system of any prior claim, wherein the sample holder comprises a Q-card, which comprises a first plate, a second plate, and spacers, wherein the spacers are configured to regulate a gap between the plates when the plates are pressed against each, compressing the sample into a thin layer.

The device, method, or system of any prior claim, wherein
the sample holder comprises a first plate, a second plate, and spacers, wherein the spacers have a uniform height and a constant inter-spacer distance; and
the sample is compressed by the sample holder into a thin layer with a uniform thickness that is regulated by the height of the spacers.

The device, method, or system of any prior claim, wherein the sample is compressed into a layer of uniform thickness that substantially equals uniform height of spacers that are fixed to one or both of the plates.

The device, method, or system of any prior claim, wherein the sample is compressed into a layer of uniform thickness that has a variation of less than 15%, 10%, 5%, 2%, 1%, or in a range between any of the two values.

The device, method, or system of any prior claim, wherein in the closed configuration, the sample has a thickness of 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, or in a range between any two of these values.

The device, method, or system of any prior claim, wherein in the closed configuration, the sample has a thickness in the range of 0.5-20 µm.

The device, method, or system of any prior claim, wherein in the closed configuration, a gap between the first plate and the second plate is 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, or in a range between any two of these values.

The device, method, or system of any prior claim, wherein the sample holder comprises a first plate and a second plate, wherein each of the plate has a thickness of 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, or in a range between any two of these values.

The apparatus, kit, or method of any prior claim, wherein the imager comprises a camera.

The apparatus, kit, or method of any prior claim, wherein the imager is a part of the detector.

The apparatus, kit, or method of any prior claim, wherein the imager is the entirety of the detector.

The apparatus, kit, or method of any prior claim, wherein the imager is directed by the software to capture one or more images of the sample, identify the interference element regions and the interference element free regions, and digitally separate the interference element regions from the interference element free regions.

The apparatus, kit, or method of any prior claim, wherein the imager comprises a filter that is configured to filter signals from the sample.

The apparatus, kit, or method of any prior claim, wherein the imager comprises a light source that is configured to illuminate the sample.

The apparatus, kit, or method of any prior claim, wherein the detector is a mobile device.

The apparatus, kit, or method of any prior claim, wherein the detector is a smart phone.

The apparatus, kit, or method of any prior claim, wherein the detector is a smart phone and the imager is a camera as part of the smart phone.

The apparatus, kit, or method of any prior claim, wherein the detector comprises a display that is configured to show the presence and/or amount of the analyte.

The apparatus, kit, or method of any prior claim, wherein the detector is configured to transmit detection results to a third party.

The apparatus, kit, or method of any prior claim, wherein the software is stored in a storage unit, which is part of the detector.

The apparatus, kit, or method of any prior claim, wherein the software is configured to direct the detector to display the presence and/or amount of the analyte.

The apparatus, kit, or method of any prior claim, wherein the software is configured to direct the imager to calculate the combined signal of the analyte from the interference element free regions.

The apparatus, kit, or method of any prior claim, wherein the software is configured to direct the imager to disregard the signal of the analyte from the interference element regions.

The apparatus, kit, or method of any prior claim, wherein the software is configured to direct the imager to increase signal contrast of the signals from the interference element regions to the signals from the interference element free regions The apparatus, kit, or method of any prior claim, wherein the software is configured to direct the detector to calculate a ratio of the signal from the interference element regions to the interference element free regions.

The device, method, or system of any prior claim, wherein the mobile apparatus is a smart phone.

The device, method, or system of any prior claim, wherein the mobile apparatus comprises a set of instructions that, when executed, direct the apparatus to capture one or more images of the sample, The device, method, or system of any prior claim, wherein the mobile apparatus comprises a light source that is configured to illuminate the sample.

The device, method, or system of any prior claim, wherein the mobile apparatus comprises a display that is configured to show the presence and/or amount of the analyte.

The device, method, or system of any prior claim, wherein the mobile apparatus comprises a set of instructions that, when executed, direct the detector to display the presence and/or amount of the analyte.

The device, method, or system of any prior claim, wherein the mobile apparatus is configured to transmit detection results to a third party.

The device, method, or system of any prior claim, wherein the adaptor comprises a filter that is configured to filter signals from the sample.

The device, method, or system of any prior claim, wherein the adaptor comprises a card slot, into which the device can be inserted.

The device, method, or system of any prior claim, wherein the adaptor comprises a slider that facilitates the insertion of the device into the card slot.

The device, method, or system of any prior claim, wherein the adaptor comprises a holder frame that is configured to removably connect to the mobile apparatus.

The device, method, or system of any prior claim, wherein the adaptor comprises an optical box that comprises one or more optical components that are configured to enhance the signal from the sample.

The device, method or system of any prior claim, wherein the apparatus or method are used for detection of proteins, peptides, nucleic acids, synthetic compounds, inorganic compounds, organic compounds, bacteria, virus, cells, tissues, nanoparticles, and other molecules, compounds, mixtures and substances thereof.

The device, method or system of any prior claim, wherein the apparatus or method are used for diagnostics, management, and/or prevention of human diseases and conditions.

The device, method or system of any prior claim, wherein the apparatus or method are used for diagnostics, management, and/or prevention of veterinary diseases and conditions, or for diagnostics, management, and/or prevention of plant diseases and conditions.

The device, method or system of any prior claim, wherein the apparatus or method are used for environments testing and decontamination.

The device, method or system of any prior claim, wherein the apparatus or method are used for agricultural or veterinary applications.

The device, method or system of any prior claim, wherein the apparatus or method are used for food testing.

The device, method or system of any prior claim, wherein the apparatus or method are used for drug testing and prevention.

The device, method or system of any prior claim, wherein the apparatus or method are used for detecting and/or measuring an analyte in blood.

The device, method or system of any prior claim, wherein the apparatus or method are used for a colorimetric assay.

The device, method or system of any prior claim, wherein the apparatus or method are used for a fluorescence assay.

The device, method or system of any prior claim, wherein the signal related to the analyte is an electrical signal or an optical signal.

The device, method or system of any prior claim, wherein the signal related to the analyte is an optical signal that allows the imager to capture images of the interference element rich region and the interference element poor region.

The device, method or system of any prior claim, wherein the signal related to the analyte is from a colorimetric reaction.

The device, method or system of any prior claim, wherein the signal related to the analyte is produced by illuminating the sample with an illumination source.

The device, method or system of any prior claim, wherein the plates are movable relative to each.

The device, method or system of any prior claim, wherein the spacers are fixed on one or both of the plates and have a uniform height.

The device, method or system of any prior claim, wherein the first plate and second plate are configured to compress the sample into a layer of uniform thickness that substantially equals the height of the spacers.

The device, method or system of any prior claim, wherein the spacers have a uniform height of 1 mm or less, 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 um or less, 0.2 um or less, 0.1 um or less, 50 nm or less, 20 nm or less, 10 nm or less, or in a range between any of the two values.

The device, method or system of any prior claim, wherein the spacers have a uniform height in the range of 0.5-2 um, 0.5-3 um, 0.5-5 um, 0.5-10 um, 0.5-20 um, 0.5-30 um, or 0.5-50 um.

The device, method or system of any prior claim, wherein at least one of the plates has a thickness of 100 mm or less, 50 mm or less, 25 mm or less, 10 mm or less, 5 mm or less, 1 mm or less, 500 um or less, 400 um or less, 300 um or less, 200 um or less, 175 um or less, 150 um or less, 125 um or less, 100 um or less, 75 um or less, 50 um or less, 40 um or less, 30 um or less, 20 um or less, 10 um or less, 5 um or less, 4 um or less, 3 um or less, 2 um or less, 1.8 um or less, 1.5 um or less, 1 um or less, 0.5 um or less, 0.2 um or less, or 0.1 um or less, or in a range between any of the two values.

The device, method or system of any prior claim, wherein at least one of the plates has a thickness in the range of 0.5 to 1.5 mm; around 1 mm; in the range of 0.15 to 0.2 mm; or around 0.175 mm.

The device, method or system of any prior claim, wherein at least one of the plates has a lateral area of 1 $mm^2$ or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, 500 $cm^2$ or less, 1000 $cm^2$ or less, 5000 $cm^2$ or less, 10,000 $cm^2$ or less, 10,000 $cm^2$ or less, or in a range between any two of these values The device, method or system of any prior claim, wherein at least one of the plates has a lateral area of in the range of 500 to 1000 $mm^2$; or around 750 $mm^2$ The device, method or system of any prior claim, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

The device, method or system of any prior claim, wherein the thickness of the flexible plate times the Young's modulus of the flexible plate is in the range 60 to 750 GPa-um.

The device, method or system of any prior claim, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $um^3/GPa$.

The device, method or system of any prior claim, wherein one or both plates comprises a location marker, either on a surface of or inside the plate, that provide information of a location of the plate.

The device, method or system of any prior claim, wherein one or both plates comprises a scale marker, either on a surface of or inside the plate, that provide information of a lateral dimension of a structure of the sample and/or the plate.

The device, method or system of any prior claim, wherein one or both plates comprises an image marker, either on a surface of or inside the plate, that assists an imaging of the sample.

The device, method or system of any prior claim, wherein the inter-spacer distance is in the range of 7 um to 50 um.

The device, method or system of any prior claim, wherein the inter-spacer distance is in the range of 50 um to 120 um.

The device, method or system of any prior claim, wherein the inter-spacer distance is in the range of 120 um to 200 um.

The device, method or system of any prior claim, wherein the spacers are pillars with a cross-sectional shape selected from round, polygonal, circular, square, rectangular, oval, elliptical, or any combination of the same.

The device, method or system of any prior claim, wherein the spacers have a pillar shape and have a substantially flat top surface, wherein, for each spacer, the ratio of the lateral dimension of the spacer to its height is at least 1.

The device, method or system of any prior claim, wherein each spacer has the ratio of the lateral dimension of the spacer to its height is at least 1.

The device, method or system of any prior claim, wherein the minimum lateral dimension of spacer is less than or substantially equal to the minimum dimension of an analyte in the sample.

The device, method or system of any prior claim, wherein the minimum lateral dimension of spacer is in the range of 0.5 um to 100 um.

The device, method or system of any prior claim, wherein the minimum lateral dimension of spacer is in the range of 0.5 um to 10 um.

The device, method or system of any prior claim, wherein the spacers have a pillar shape, and the sidewall corners of the spacers have a round shape with a radius of curvature at least 1 μm.

The device, method or system of any prior claim, wherein the spacers have a density of at least $100/mm^2$.

The device, method or system of any prior claim, wherein the spacers have a density of at least $1000/mm^2$.

The device, method or system of any prior claim, wherein at least one of the plates is transparent The device, method or system of any prior claim, wherein at least one of the plates is made from a flexible polymer.

The device, method or system of any prior claim, wherein, for a pressure that compresses the plates, the spacers are not compressible and/or, independently, only one of the plates is flexible.

The device, method or system of any prior claim, wherein the flexible plate has a thickness in the range of 10 um to 200 um.

The device, method or system of any prior claim, wherein the variation of sample thickness is less than 30%.

The device, method or system of any prior claim, wherein the variation of sample thickness is less than 10%.

The device, method or system of any prior claim, wherein the variation of sample thickness is less than 5%.

The device, method or system of any prior claim, wherein the first and second plates are connected and are configured to be changed from the open configuration to the closed configuration by folding the plates.

The device, method or system of any prior claim, wherein the first and second plates are connected by a hinge and are configured to be changed from the open configuration to the closed configuration by folding the plates along the hinge.

The device, method or system of any prior claim, wherein the first and second plates are connected by a hinge that is a separate material to the plates, and are configured to be changed from the open configuration to the closed configuration by folding the plates along the hinge.

The device, method or system of any prior claim, wherein the first and second plates are made in a single piece of material and are configured to be changed from the open configuration to the closed configuration by folding the plates.

The device, method or system of any prior claim, wherein the layer of uniform thickness sample is uniform over a lateral area that is at least 1 $mm^2$.

The device, method or system of any prior claim, wherein the spacers are fixed on a plate by directly embossing the plate or injection molding of the plate.

The device, method or system of any prior claim, wherein the materials of the plate and the spacers are selected from polystyrene, PMMA, PC, COC, COP, or another plastic.

(1) Definitions

The terms used in describing the devices/apparatus, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(2) Sample

The devices/apparatus, systems, and methods herein disclosed can be applied to manipulation and detection of various types of samples. The samples are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that comprises cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample comprises raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (μL, "uL" herein) or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values.

In some embodiments, the volume of the sample includes, but is not limited to, about 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values. In some embodiments, the volume of the sample includes, but is not limited to, about 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

(3) Q-Card, Spacers and Uniform Sample Thickness

The devices/apparatus, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In essence, the term "spacers" or "stoppers" can refer to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

(4) Hinges, Opening Notches, Recessed Edge and Sliders

The devices/apparatus, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

(5) Q-Card and Adaptor

The devices/apparatus, systems, and methods herein disclosed can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension and connection of the Q-card, the adaptor, and the mobile are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

(6) Smartphone Detection System

The devices/apparatus, systems, and methods herein disclosed can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a Zig Bee network, a near field communication (NFC) network, or the like, or any combination thereof.

In some embodiments, the smartphone is an iPhone™, an Android™ phone, or a Windows™ phone.

(7) Detection Methods

The devices/apparatus, systems, and methods herein disclosed can include or be used in various types of detection methods. The detection methods are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287, 62/456,528, 62/456631, 62/456522, 62/456598, 62/456603, and 62/456,628, which were filed on Feb. 8, 2017, U.S. Provisional Application Nos. 62/459,276, 62/456,904, 62/457075, and 62/457,009, which were filed on Feb. 9, 2017, and U.S. Provisional Application Nos. 62/459,303, 62/459,337, and 62/459,598, which were filed on Feb. 15, 2017, and U.S. Provisional Application Nos. 62/460,083, 62/460,076, which were filed on Feb. 16, 2017, all of which applications are incorporated herein in their entireties for all purposes.

(8) Labels, Capture Agent and Detection Agent

The devices/apparatus, systems, and methods herein disclosed can employ various types of labels, capture agents, and detection agents that are used for analytes detection. The labels are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylam inophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144;

IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from Anthozoan species; combinations thereof; and the like.

In any embodiment, the QMAX device can contain a plurality of capture agents and/or detection agents that each bind to a biomarker selected from Tables B1, B2, B3 and/or B7 in U.S. Provisional Application No. 62/234,538 and/or PCT Application No. PCT/US2016/054025, wherein the reading step d) includes obtaining a measure of the amount of the plurality of biomarkers in the sample, and wherein the amount of the plurality of biomarkers in the sample is diagnostic of a disease or condition.

In any embodiment, the capture agent and/or detection agents can be an antibody epitope and the biomarker can be an antibody that binds to the antibody epitope. In some embodiments, the antibody epitope includes a biomolecule, or a fragment thereof, selected from Tables B4, B5 or B6 in U.S. Provisional Application No. 62/234,538 and/or PCT Application No. PCT/US2016/054025. In some embodiments, the antibody epitope includes an allergen, or a fragment thereof, selected from Table B5. In some embodiments, the antibody epitope includes an infectious agent-derived biomolecule, or a fragment thereof, selected from Table B6 in U.S. Provisional Application No. 62/234,538 and/or PCT Application No. PCT/US2016/054025.

In any embodiment, the QMAX device can contain a plurality of antibody epitopes selected from Tables B4, B5 and/or B6 in U.S. Provisional Application No. 62/234,538 and/or PCT Application No. PCT/US2016/054025, wherein the reading step d) includes obtaining a measure of the amount of a plurality of epitope-binding antibodies in the sample, and wherein the amount of the plurality of epitope-binding antibodies in the sample is diagnostic of a disease or condition.

(9) Analytes

The devices/apparatus, systems, and methods herein disclosed can be applied to manipulation and detection of various types of analytes (including biomarkers). The analytes are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application No. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipet, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

(10) Applications

The devices/apparatus, systems, and methods herein disclosed can be used for various applications (fields and samples). The applications are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

(11) Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

In some embodiments, the dimensions are listed in the Tables below:

| | Plates: | |
|---|---|---|
| Parameters | Embodiments | Preferred Embodiments |
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 $mm^2$; or around 750 $mm^2$. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

| | Hinge: | |
|---|---|---|
| Parameters | Embodiments | Preferred Embodiments |
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |

| Hinge: | | |
|---|---|---|
| Parameters | Embodiments | Preferred Embodiments |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm$^2$ or less, 5 mm$^2$ or less, 10 mm$^2$ or less, 20 mm$^2$ or less, 30 mm$^2$ or less, 40 mm$^2$ or less, 50 mm$^2$ or less, 100 mm$^2$ or less, 200 mm$^2$ or less, 500 mm$^2$ or less, or in a range between any of the two values | In the range of 20 to 200 mm$^2$; or about 120 mm$^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or Around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

| Notch: | | |
|---|---|---|
| Parameters | Embodiments | Preferred Embodiments |
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 mm$^2$ (square millimeter) or less, 10 mm$^2$ or less, 25 mm$^2$ or less, 50 mm$^2$ or less, 75 mm$^2$ or less or in a range between any two of these values. | In the range of 10 to 150 mm$^2$; or about 50 mm$^2$ |

| Trench: | | |
|---|---|---|
| Parameters | Embodiments | Preferred Embodiments |
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 $mm^2$ or less, 0.005 $mm^2$ or less, 0.01 $mm^2$ or less, 0.05 $mm^2$ or less, 0.1 $mm^2$ or less, 0.5 $mm^2$ or less, 1 $mm^2$ or less, 2 $mm^2$ or less, 5 $mm^2$ or less, 10 $mm^2$ or less, 20 $mm^2$ or less, or in a range between any two of these values. | |
| Volume | 0.1 uL or more, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

25

| Receptacle Slot | | |
|---|---|---|
| Parameters | Embodiments | Preferred Embodiments |
| Shape of receiving area | round, ellipse, rectangle, triangle, polygon, ring-shaped, or any superposition of these shapes; | |
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |
| Difference between receiving area and card area | 1 $mm^2$ (square millimeter) or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, or in a range between any of the two values. | |

(12) Cloud

The devices/apparatus, systems, and methods herein disclosed can employ cloud technology for data transfer, storage, and/or analysis. The related cloud technologies are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

OTHER EMBODIMENTS

Further examples of inventive subject matter according to the present disclosure are described in the following enumerated paragraphs.

It must be noted that, as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" or "approximately" can mean within an acceptable error range for the particular value as determined by one of ordinary skill in the art, which will depend in part on how the value is measured or determined, e.g. the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In certain embodiments, the term "about" can refer to ±10%. In certain embodiments, the term "about" can refer to ±5%.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") can refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, e.g., "one or more" of the entity so conjoined. Other entity can optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

What is claimed is:

1. A device comprising:
   a first plate, a second plate, a light guiding spacer (LGS), a sampling region, and a reference region, wherein:
   (i) the first plate and second plate are configured to sandwich a sample, this is for an optical transmission analysis by light, into a thin layer between the plates, and each plate has a sample contact area on its inner surface that contacts the sample;
   (ii) the light-guiding spacer (LGS) has a pillar shape, is sandwiched between the two plates with each end of the light-guiding spacer (LGS) in direct contact to one of the plates forming a LGS-plate contact area, and is configured to allow the light to transmit from the first plate, through the LGS, to the second plate without going through a sample,
   (iii) the sampling region is the region that the light can go through, in sequence, the first plate, the sample, and the second plate, wherein the sampling region does not have the LGS; and
   (iv) the reference region is the region that the light transmits through, in sequence, the first plate, the light-guiding spacer, and the second plate, without going through the sample;
   wherein the LGS-plate contact areas and a lateral cross-section of the LGS are larger than the wavelength of the light,
   wherein the light-guiding spacer is surrounded by or near the sample; and
   wherein the sample in the sampling region has a thickness of 500 um or less.

2. An apparatus for sample analysis, comprising:
   a device of claim 1, a light source, a camera; and an adaptor, wherein
   (i) the light source is configured to emit light in the wavelength range that is configured to go through the reference region;

(ii) the camera is configured to image the reference region and the sampling region;

(iii) the adaptor is configured to position the device, the light source, and the camera relative to each other, so that the light from the light source goes through the reference region and the sampling region and is imaged by the camera.

3. The apparatus of claim 2, further comprising:
a processor, which is configured to process the images captured by the camera, and determine a property of the analyte in the sample based on comparing light transmissions from the reference region and the sampling region.

4. The apparatus of claim 2, wherein the camera and the processor are parts of a single mobile device.

5. The apparatus of claim 2, wherein the light source and the processor are parts of a single mobile device.

6. The apparatus of claim 2, wherein the light source, the camera, and the processor are parts of a single mobile device.

7. The apparatus of claim 2, wherein the mobile device is a smart phone.

8. A method for sample analysis using an transmitted light,
comprising the steps of:
(a) having a device of claim 1;
(b) depositing the sample at the open configuration of the device, wherein the sample is suspected of containing an analyte;
(c) bringing the device into the closed configuration;
(d) having a light source that has a wavelength that is configured to go through the reference region of the device;
(e) having an imager that is configured to image the reference region and the sampling region of the device;
(f) having an adaptor that is configured to position the device, the light source, and the camera relative to each other, so that the light from the light source goes through the reference region and the sampling region and is imaged by the camera;
(g) determining a property of the analyte by comparing the light transmission from the sampling region and the reference region.

9. The device of claim 1, wherein the analyte is hemoglobin.

10. The device of claim 1, wherein the analyte is type of cells.

11. The device of claim 1, wherein the thickness of the sample layer is regulated by plates and the light-guiding spacers and is substantially the same as the uniform height of the light-guiding spacers.

12. The device of claim 1, wherein the analyte is red blood cells.

13. The device of claim 1, wherein the analyte is white blood cells.

14. The device of claim 1, wherein the reference region and the sampling region have a same size.

15. The device of claim 1, wherein the reference region is within a corresponding area of the cross section of the light-guide spacer.

16. The device of claim 1, wherein the reference region is less than 0.1 um^2, less than 0.2 um^2, less than 0.5 um^2, less than 1 um^2, less than 2 um^2, less than 5 um^2, less than 10 um^2, less than 20 um^2, less than 50 um^2, less than 100 um^2, less than 200 um^2, less than 500 um^2, less than 1000 um^2, less than 2000 um^2, less than 5000 um^2, less than 10000 um^2, less than 20000 um^2, less than 50000 um^2, less than 100000 um^2, less than 200000 um^2, less than 500000 um^2, less than 1 mm^2, less than 2 mm^2, less than 5 mm^2, less than 10 mm^2, less than 20 mm^2, or less than 50 mm^2, or in a range between any of the two values.

17. The device of claim 1, wherein the device further comprises a plurality of light guiding spacers that have substantially uniform height, and wherein at least one of the light-guiding spacers is inside the sample contact area.

18. The device of claim 1, wherein the device further comprises a plurality of light guiding spacers that have substantially uniform height, wherein the distance between two neighboring light guiding spacers are known, and wherein at least one of the light-guiding spacers is inside the sample contact area.

19. The device of claim 1, wherein the device further comprises a plurality of light guiding spacers that have substantially uniform height, wherein the distances between two neighboring light guiding spacers are known and are substantially constant (i.e. the light guiding spacers are substantially a periodic array), and wherein at least one of the light-guiding spacers is inside the sample contact area.

20. The device of claim 1, wherein the bottom surface of the light guiding spacer is fixed on the inner surface of one of the plates by molding the light guiding spacer on the inner surface of the plate.

21. The device of claim 1, wherein the bottom surface of the light guiding spacer is fixed on the inner surface of one of the plates and is made of the same material as the inner surface.

22. The device of claim 1, wherein the bottom surface of the light guiding spacer is fixed on the inner surface of one of the plates, and is made of the same material as the inner surface, and the bottom surface of the light guiding spacer has no interface with on the inner surface of the plate.

23. The device of claim 1, wherein the wavelength of the light is longer than 300 nm, and wherein the wavelength of the light is also less than 20 μm, less than 15 μm, less than 10 μm, less than 5 μm, less than 4 μm, less than 3 μm, less than 2 μm, less than 1 μm, less than 800 nm, less than 750 nm, less than 700 nm, less than 650 nm, less than 600 nm, less than 550 nm, less than 500 nm, less than 450 nm, less than 400 nm, or in a range between any of the two values.

24. The device of claim 1, wherein the wavelength of the light is longer than 500 nm, and wherein the wavelength of the light is also less than 600 nm, less than 590 nm, less than 580 nm, less than 570 nm, less than 560 nm, less than 550 nm, less than 540 nm, less than 530 nm, less than 520 nm, less than 510 nm, or in a range between any of the two values.

25. The device of claim 1, wherein the average lateral cross-section of each light-guiding spacer is less than 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, 500,000 um^2, 1 mm^2, 2 mm^2, 5 mm^2, 10 mm^2, 50 mm^2, or in a range between any of the two values.

26. The device of claim 1, wherein the average lateral cross-section of each light-guiding spacer is less than 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, or in a range between any of the two values.

27. The device of claim 1, wherein the average lateral cross-section of each light-guiding spacer is less than 1 um^2

(micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, or in a range between any of the two values.

28. The device of claim 1, wherein the sample contact area is larger than 100 um^2(micron-square), larger than 200 um^2, larger than 400 um^2, larger than 600 um^2, larger than 800 um^2, larger than 1,000 um^2, larger than 2,000 um^2, larger than 4,000 um^2, larger than 6,000 um^2, larger than 8,000 um^2, larger than 10,000 um^2, larger than 20,000 um^2, larger than 40,000 um^2, larger than 60,000 um^2, larger than 80,000 um^2, larger than 100,000 um^2, larger than 200,000 um^2, larger than 250,000 um^2, larger than 500,000 um^2(micron-square), or in a range between any of the two values.

29. The device of claim 1, wherein a predetermined constant inter-spacer distance that is at least about 2 times larger than the size of the analyte.

30. The device of claim 1, wherein a predetermined constant inter-spacer distance that is larger than the size of the analyte by a factor that is at least 2 times, at least 6 times, at least 8 times, at least 10 times, at least 20 times, at least 40 times, at least 60 times, at least 80 times, or at least 100 times.

31. The device of claim 1, wherein the height of light-guiding spacer is 1 um, 2 um, 5 um, 10 um, 30 um, 50 um, 100 um, 200 um, 500 um, 1,000 um, 2,000 um, 5,000 um, 10,000 um, or in a range between any of the two values.

32. The device of claim 1, wherein the spacers are arranged in periodic array with a period of 1 um, 2 um, 5 um, 10 um, 30 um, 50 um, 100 um, 200 um, 500 um, 1,000 um, 2,000 um, 5,000 um, 10,000 um, or in a range between any of the two values.

33. The device of claim 1, wherein the LGS has a pillar shape with its ends substantially flat.

34. The device of claim 1, wherein one or both of the ends of the LGS are fixed with one or both of the plates by bonding, fusing, made from a single piece, or other methods that connect LGS to the plates.

35. The device of claim 1, wherein the shape of the lateral cross-section of LGS includes, not limited to circular, rectangle, square, triangle, polygon, alphabets, numbers, or a combination of thereof.

36. The device of claim 1, wherein the average lateral cross-section of each light-guiding spacer is larger than the wavelength of the light that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

37. The device of claim 1, wherein the average lateral cross-section of each light-guiding spacer is larger than the wavelength of the light that goes through the reference region, by 1 fold, 2 fold, 3 fold, 5 fold, 10 fold, 20 fold, 50 fold, 100 fold, 200 fold, 500 fold, or in a range between any of the two values.

38. The device of claim 1, wherein the reference region is less than the size of the minimum lateral cross-section of the light guiding pillar, One advantage is to avoid or reduce light scattering the light guiding sidewall to affect the reference signal.

39. The device of claim 1, wherein the minimum distance between the edge of the light guiding spacer and that of the reference region is 1 um (micron), 2 um, 3 um, 5 um, 10 um, 20 um, 30 um, 50 um, 100 um, 200 um, 500 um, 1000 um, or in a range between any of the two values.

40. The device of claim 1, wherein the minimum distance between the edge of the light guiding spacer and that of the reference region is 1 um (micron), 2 um, 3 um, 5 um, 10 um, 20 um, 30 um, 50 um, 100 um, 200 um, or in a range between any of the two values.

41. The device of claim 1, wherein the minimum distance between the edge of the light guiding spacer and that of the reference region is 1 um (micron), 2 um, 3 um, 5 um, 10 um, 20 um, 30 um, 50 um, or in a range between any of the two values.

42. The device of claim 1, wherein the ratio of the reference region area and the light guiding spacer area is 3/10, 2/5, 1/2, 3/5, 7/10, 4/5, or in a range between any of the two values.

43. The device of claim 1, wherein the edge of the sampling region is a distance away from the edge of the light guiding pillar.

44. The device of claim 1, wherein the area of the sampling region is 3/5, 7/10, 4/5, 9/10, 1, 11/10, 6/5, 13/10, 7/5, 3/2, or in the range between any of the two values, of the periodic inter spacer distance.

45. The device of claim 1, wherein the distance between the edge of the sampling region and that of the light guiding spacer is 1/5, 3/10, 2/5, 1/2, 3/5, 7/10, 4/5, 9/10, 1, or in the rage between any of the two values, of the light guiding spacer area.

46. The device of claim 1, wherein the distance between the edge of the sampling region and that of the light guiding spacer is larger than the wavelength, that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

47. The device of claim 1, wherein the distance between the edge of sampling area and the reference region is 1 um (micron), 2 um, 3 um, 5 um, 10 um, 20 um, 30 um, 40 um, 50 um, 100 um, 200 um, 500 um, 1000 um or in the range between any of the two values.

48. The device of claim 1, wherein the distance between the edge of sampling area and the reference region is from 30 um (micron) to 50 um, 20 um to 60 um, 10 um to 70 um, 5 um to 75 um, or in the range between any of the two values.

49. The device of claim 1, wherein the distance between the edge of sampling area and the reference region is larger than the wavelength, that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

50. The device of claim 1, wherein the distance between the edge of sampling area and the reference region is 2/5, 1/2, 3/5, 7/10, 4/5, 9/10, 1, 11/10, 6/5, 13/10, 7/5, 3/2, 8/5, 17/10, or in the range between any of the two values, of the light guiding spacer area.

51. The device, apparatus, or method of claim 1, wherein the analyte is a biomarker, an environmental marker, or a foodstuff marker.

52. The device of claim 1, wherein the analyte is a biomarker indicative of the presence or severity of a disease or condition.

53. The device of claim 1, wherein the analyte is a cell, a protein, or a nucleic acid.

54. The device of claim 1, wherein the analyte comprises proteins, peptides, nucleic acids, synthetic compounds, inorganic compounds, organic compounds, bacteria, virus, cells, tissues, nanoparticles, and other molecules, compounds, mixtures and substances thereof.

55. The device of claim 1, wherein the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

56. The device of claim 1, wherein the sample is original, diluted, or processed forms of blood.

57. The device of claim 1, wherein the sample comprises whole blood.

58. The device of claim 1, wherein the inter spacer distance (SD) is equal or less than about 150 um (micrometer).

59. The device of claim 1, wherein the inter spacer distance (SD) is equal or less than about 100 um (micrometer).

60. The device of claim 1, wherein the fourth power of the inter-spacer-distance (ISD) divided by the thickness (h) and the Young's modulus (E) of the flexible plate (ISD$^4$/(hE)) is $5\times10^6$ um$^3$/GPa or less.

61. The device of claim 1, wherein the fourth power of the inter-spacer-distance (ISD) divided by the thickness (h) and the Young's modulus (E) of the flexible plate (ISD$^4$/(hE)) is $5\times10^5$ um$^3$/GPa or less.

62. The device of claim 1, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

63. The device of claim 1, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is $5\times10^6$ um$^3$/GPa or less.

64. The device of any prior device claim 1, wherein the ratio of the inter-spacing distance of the spacers to the average width of the spacer is 2 or larger, and the filling factor of the spacers multiplied by the Young's modulus of the spacers is 2 MPa or larger.

65. The device of claim 1, wherein one or both plates comprises a location marker, either on a surface of or inside the plate, that provide information of a location of the plate.

66. The device of claim 1, wherein one or both plates comprises a scale marker, either on a surface of or inside the plate, that provide information of a lateral dimension of a structure of the sample and/or the plate.

67. The device of claim 1, wherein one or both plates comprises an image marker, either on a surface of or inside the plate that assists an imaging of the sample.

68. The device of claim 1, wherein the sample is a biological sample, a chemical sample, an environmental sample, or a foodstuff sample.

69. A device for analyzing hemoglobin in a sample, comprising:
a first plate, a second plate, and a light-guiding spacer, wherein:
(i) the first plate and second plate are movable relative to each other into different configurations, including an open configuration and a closed configuration;
(ii) each of the plates comprises an inner surface that has a sample contact area for contacting a sample that contains or is suspected to contain hemoglobin; and
(iii) the light-guiding spacer has a pillar shape, wherein top and bottom surfaces of the light-guiding spacers are substantially flat and the bottom surface is fixed on the inner surface of one of the plates, wherein the area of the top and bottom surfaces and average lateral cross-section of each spacer is respectively larger than the wavelength of the light that analyzes the sample, wherein the light-guiding spacer is inside the sample contact area;
wherein the open configuration is a configuration, in which: the two plates are separated apart, the spacing between the plates is not regulated by the light-guiding spacers, and the sample is deposited on one or both of the plates;
wherein the closed configuration is a configuration, which is configured after the sample deposition in the open configuration; and in the closed configuration: at least part of the sample is compressed by the two plates into a layer of highly uniform thickness, wherein the uniform thickness of the layer is confined by the sample contact areas of the plates and is regulated by the plates and the light-guiding spacers; and
wherein in the closed configuration: (a) at least one spacer in the sample contact area has its top surface in direct contact with one of the plates, and the at least one spacer and the regions of the plates above and below the at least one spacer define a reference region wherein the reference region is transparent to light within a wavelength range, and (b) at least one region in the sample contact area on one plate and its corresponding region on the other plate are not occupied by the light-guiding spacers, defining a sampling region that is transparent to light within the same wavelength range.

70. The device of claim 69, wherein the average lateral cross-section of each light-guiding spacer (LGS) is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, 500,000 um^2, 1 mm^2, 2 mm^2, 5 mm^2, 10 mm^2, 50 mm^2, or in a range between any of the two values.

71. The device of claim 69, wherein the average lateral cross-section of each light-guiding spacer is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, 100,000 um^2, 200,000 um^2, or in a range between any of the two values.

72. The device of claim 69, wherein the average lateral cross-section of each light-guiding spacer is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, 10,000 um^2, 30,000 um^2, or in a range between any of the two values.

73. The device of claim 69, wherein the average lateral cross-section of each light-guiding spacer is 1 um^2 (micron-square), 10 um^2, 20 um^2, 30 um^2, 50 um^2, 100 um^2, 150 um^2, 200 um^2, 300 um^2, 500 um^2, 1000 um^2, 2000 um^2, 5000 um^2, or in a range between any of the two values.

74. The device of claim 69, wherein the minimum distance between the edge of the light guiding spacer and that of the reference region is larger than the wavelength, that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

75. The device of claim 69, wherein the distance between the edge of the sampling region and that of the light guiding spacer is larger than the wavelength, that goes through the sampling region, by 1 fold, 2 fold, 3 fold, 5 fold, 10 fold, 20 fold, 50 fold, 100 fold, 200 fold, 500 fold, 1000 fold, 5000 fold or in a range between any of the two values.

76. The device of claim 69, wherein the distance between the edge of sampling area and the reference region is larger than the wavelength of the light that goes through the reference region, by 1 fold, 2 fold, 3 fold, 5 fold, 10 fold, 20 fold, 50 fold, 100 fold, 200 fold, 500 fold, 1000 fold, 5000 fold or in a range between any of the two values.

77. The device of claim 69, wherein the analyte is hemoglobin.

78. The device of claim 69, wherein the sample is original, diluted, or processed forms of: bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, or exhaled breath condensate.

79. The device of claim 69, wherein the sample is original, diluted, or processed forms of blood.

80. The device of claim 69, wherein the sample comprises whole blood.

81. A device for analyzing hemoglobin in an analyte in a sample, comprising:
 a first plate, a second plate, and a light-guiding spacer, wherein:
  (i) the first plate and second plate are configured to hold a sample that contains or is suspected to contain an analyte, wherein at least part the sample is between the two plates and is in contact with both plates; and
  (ii) the light-guiding spacer has a pillar shape and a predetermined substantially uniform height,
 wherein top and bottom surfaces of the light-guiding spacers are substantially flat and the top and bottom surfaces of at least one spacer are in direct contact with the plates,
 wherein the area of the top and bottom surfaces and average lateral cross-section of each spacer is respectively larger than the wavelength of the light that analyze the sample, and
 wherein: (a) the at least one spacer and the regions of the plates directly above and below the at least one spacer define a reference region that is transparent to light within a wavelength range and passing through the plates and the spacer, and (b) at least one region in the sample contact area on one plate and its corresponding region on the other plate are not occupied by the light-guiding spacers, defining a sampling region that is transparent to light within the same wavelength range.

82. The device of claim 81, wherein the minimum distance between the edge of the light guiding spacer and that of the reference region is larger than the wavelength, that goes through the sampling region, by 1 fold, 2 fold, 3 fold, 5 fold, 10 fold, 20 fold, 50 fold, 100 fold, 200 fold, 500 fold, 1000 fold, 5000 fold or in a range between any of the two values.

83. The device of claim 81, wherein the distance between the edge of sampling area and the reference region is larger than the wavelength, that goes through the sampling region, by 1 fold, 2 fold, 3 fold, 5 fold, 10 fold, 20 fold, 50 fold, 100 fold, 200 fold, 500 fold.

84. A device for analyzing an analyte in a sample, comprising:
 a first plate, a second plate, and light-guiding spacers, wherein:
  (i) the first plate and second plate are movable relative to each other into different configurations, including an open configuration and a closed configuration;
  (ii) each of the plates comprises an inner surface that has a sample contact area for contacting a sample that contains or is suspected to contain an analyte; and
  (iii) the light-guiding spacers have a pillar shape and a predetermined substantially uniform height, wherein top and bottom surfaces of the light-guiding spacers are substantially flat and the bottom surface is fixed on the inner surface of one or the plates, wherein the area of the top and bottom surfaces and average lateral cross-section of each spacer is respectively larger than the wavelength of the light that analyzes the sample, wherein at least one of the light-guiding spacers is inside the sample contact area;
 wherein the open configuration is a configuration, in which: the two plates are separated apart, the spacing between the plates is not regulated by the light-guiding spacers, and the sample is deposited on one or both of the plates;
 wherein the closed configuration is a configuration, which is configured after the sample deposition in the open configuration; and in the closed configuration: at least part of the sample is compressed by the two plates into a layer of highly uniform thickness, wherein the uniform thickness of the layer is confined by the sample contact areas of the plates and is regulated by the plates and the light-guiding spacers; and
 wherein in the closed configuration, (a) at least one spacer in the sample contact area has its top surface in direct contact with one of the plates, and the at least one spacer and the regions of the plates above and below the at least one spacer define a reference region wherein the reference region is transparent to light within a wavelength range, and (b) at least one region in the sample contact area on one plate and its corresponding region on the other plate are not occupied by the light-guiding spacers, defining a sampling region that is transparent to the light within the wavelength range.

\* \* \* \* \*